(12) United States Patent
Migawa et al.

(10) Patent No.: US 6,933,288 B2
(45) Date of Patent: Aug. 23, 2005

(54) PYRANOSYL CYTOSINES: PHARMACEUTICAL FORMULATIONS AND METHODS

(75) Inventors: Michael T. Migawa, San Marcos, CA (US); Eric E. Swayze, Carlsbad, CA (US); Richard H. Griffey, Vista, CA (US)

(73) Assignee: ISIS Pharmaceuticals, Inc., Carlsbad ( * ) Notice: Subject to any disclaimer, the term of this patent is extended or adjusted under 35 U.S.C. 154(b) by 200 days.

(21) Appl. No.: 10/067,017

(22) Filed: Feb. 4, 2002

(65) Prior Publication Data

US 2003/0216575 A1 Nov. 20, 2003

(51) Int. Cl.[7] ............... C07D 407/04; C07H 19/06; A61K 31/506; A61K 31/7068
(52) U.S. Cl. ............... 514/49; 536/28.5; 536/28.52; 536/28.4; 544/317
(58) Field of Search ............... 514/49; 536/28.5, 536/28.52, 28.4; 544/317

(56) References Cited

PUBLICATIONS

Cheney, B. V., et al., "A. B. Structural comparisons of antibiotic inhibitors of peptidyltransferase," Theochem 1986, 27, 389–400.

Clark, J. M., Jr. "Gougerotin," Antibiotica 1967, 1, 278–282.

Coutsogeorgopoulos, C., et al., "Synthetic studies on nucleoside antibiotics. 13. Inhibitors of protein synthesis. 4. Structure–activity relation of gougerotin and some of its analogs," J. Med. Chem., 1975, 18, 771–776.

Epp, J. B., et al., "Facile Preparation of Nucleoside–5'–carboxylic Acids," J. Org. Chem. 1999, 64, 293–295.

Fang, L., et al. "Evaluation of evaporative light–scattering detector for combinatorial library quantitation by reversed phase HPLC," J. Comb. Chem. 2000, 2, 254–257.

Forman, F. W., et al., "Sucholeiki, I. Solid–Phase Synthesis of Biaryls via the Stille Reaction," J. Org. Chem. 1995, 60, 523–528.

Larhed, M., et al., "A. Rapid microwave–assisted Suzuki coupling on solid–phase," Tetrahedron Lett., 1996, 37, 8219–8222.

Lichtenhaler, F. W., et al., "Total synthesis of 'aspiculamycin' and gougerotin " Nucleic Acids Res., Spec. Publ., 1975, 1, S33–S36.

Plunkett, M. J., et al., "Solid–Phase Synthesis of Structurally Diverse 1,4–Benzodiazepine Derivatives Using the Stille Coupling Reaction," J. Am. Chem. Soc., 1995, 117, 3306–3307.

Shute, R. E., et al., "Synthesis and evaluation of novel activated mixed carbonate reagents for the introduction of the 2–(trimethylsilyl)ethoxycarbonyl (Teoc) protecting group," Synthesis, 1987, 346–349.

Takahashi, A., et al., "A and B, new nucleoside antibiotics produced by a strain of Bacillus circulans. I. Taxonomy of the producing organism and isolation and biological properties of the antibiotics," J. Antibiot. 1986, 39, 1033–1040.

Takahashi, A et al., "A and B, new nucleoside antibiotics produced by a strain of Bacillus circulans. II. Physicochemical properties and structure determination," J. Antibiot. 1986, 39, 1041–1046.

Vorbrueggen, H., "Adventures in Silicon–Organic Chemistry," Acc. Chem. Res., 1995, 28, 509–520.

Ward, Y. D., et al., "Solid phase synthesis of aryl amines via palladium catalyzed amination of resin–bound aromatic bromides," Tetrahedron Lett. 1996, 37, 6993–6996.

Watanabe, K. A, et al., "Nucleosides. LXXV. Synthetic studies on nucleoside antibiotics. 9. Total synthesis of gougerotin," J. Amer. Chem. Soc. 1972, 94, 3272–3274.

Watanabe, K. A., et al., "Nucleosides. LXIII. Synthetic studies on nucleoside antibiotics. Total syntheses of 1–(4–amino–4–deoxy–.beta.–D–glucopyranosyluronic acid)cytosine, the nucleoside moiety of gougerotin," J. Org. Chem., 1970, 35, 231–236.

*Primary Examiner*—Thomas C. McKenzie
(74) *Attorney, Agent, or Firm*—Woodcock Washburn LLP

(57) ABSTRACT

This invention is directed to novel pyranosyl cytosine compounds depicted graphically as structure I. This invention is further directed to a unique methodology for their preparation using solid-phase methodology. These hexopyranosyl cytosine derived natural product analogs share their parent compounds broad-spectrum antimicrobial and anti-fungal profile and represent a vast, novel compound class of 50S rRNA directed inhibitors of protein translation.

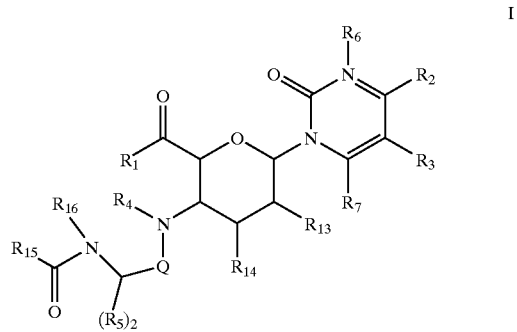

41 Claims, No Drawings

PYRANOSYL CYTOSINES: PHARMACEUTICAL FORMULATIONS AND METHODS

FIELD OF THE INVENTION

This invention is directed to novel pyranosyl cytosine compounds depicted graphically as structure I. This invention is further directed to a unique methodology for their preparation using solid-phase methodology. These hexopyranosyl cytosine derived natural product analogs share their parent compounds broad-spectrum antimicrobial and antifungal profile and represent a vast, novel compound class of 50S rRNA directed inhibitors of protein translation.

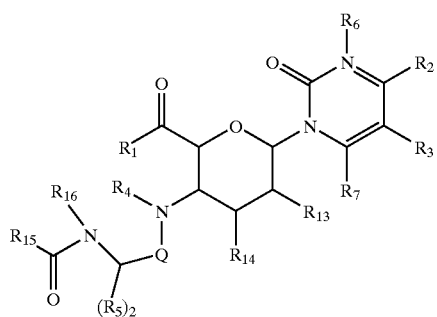

I

INTRODUCTION AND BACKGROUND

Gougerotin, depicted graphically as structure II, has been obtained either by isolation from the fermentation broth of *Streptomyces gougeroti* or through total synthesis (Takahashi, A.; Ikeda, D.; Naganawa, H.; Okami, Y.; Umezawa, H. Bagougeramines A and B, new nucleoside antibiotics produced by a strain of Bacillus circulans. II. Physico-chemical properties and structure determination. *J. Antibiot.* 1986, 39, 1041–1046. And Takahashi, A.; Saito, N.; Hotta, K.; Okami, Y.; Umezawa, H. Bagougeramines A and B, new nucleoside antibiotics produced by a strain of Bacillus circulans. I. Taxonomy of the producing organism and isolation and biological properties of the antibiotics. *J. Antibiot.* 1986, 39, 1033–1040). No semi-synthetic analogs have been reported in the literature, and only about thirty analogs based on the total synthesis have been reported. The naturally occurring pyranosyl cytosines represent a class of several natural products that share a broad-spectrum antimicrobial profile (Cheney, B. V.; Miller, A. B. Structural comparisons of antibiotic inhibitors of peptidyltransferase. *Theochem* 1986, 27, 389–400). Among the pyranosyl cytosines is gougerotin as depicted in structure II, a naturally occurring compound that is closely related to the bagougeramines (Clark, J. M., Jr. Gougerotin. *Antibiotica* 1967, 1, 278–282; Lichtenthaler, F. W.; Morino, T.; Winterfeldt, W. Total synthesis of 'aspiculamycin' and gougerotin. *Nucleic Acids Res., Spec. Publ.* 1975, 1, S33–S36;). In general, this class shares a related hexopyranosyl cytosine moiety connected to a modified peptidic side-chain.

Few analogs to Gougerotin have been made and no useful, pharmaceutically significant semi-synthetic analogs have been reported (Takahashi, A.; Ikeda, D.; Naganawa, H.; Okami, Y.; Umezawa, H. Bagougeramines A and B, new nucleoside antibiotics produced by a strain of *Bacillus circulans*. II. Physico-chemical properties and structure determination. J. Antibiot. 1986, 39, 1041–1046; Takahashi, A.; Saito, N.; Hotta, K.; Okami, Y.; Umezawa, H. Bagougeramines A and B, new nucleoside antibiotics produced by a strain of *Bacillus circulans*. I. Taxonomy of the producing organism and isolation and biological properties of the antibiotics. J. Antibiot. 1986, 39, 1033–1040; Cheney, B. V.; Miller, A. B. Structural comparisons of antibiotic inhibitors of peptidyltransferase. Theochem 1986, 27, 389–400; Clark, J. M., Jr. Gougerotin. Antibiotica 1967, 1, 278–282; Lichtenthaler, F. W.; Morino, T.; Winterfeldt, W. Total synthesis of 'aspiculamycin' and gougerotin. Nucleic Acids Res., Spec. Publ. 1975, 1, S33–S36; Watanabe, K. A.; Falco, E. A.; Fox, J. J. Nucleosides. LXXV. Synthetic studies on nucleoside antibiotics. 9. Total synthesis of gougerotin. J. Amer. Chem. Soc. 1972, 94, 3272–3274; Coutsogeorgopoulos, C.; Bloch, A.; Watanabe, K. A.; Fox, J. J. Synthetic studies on nucleoside antibiotics. 13. Inhibitors of protein synthesis. 4. Structure-activity relation of gougerotin and some of its analogs. J. Med. Chem. 1975, 18, 771–776; Watanabe, K. A.; Kotick, M. P.; Fox, J. J. Nucleosides. LXIII. Synthetic studies on nucleoside antibiotics. Total syntheses of 1-(4-amino-4-deoxy-.beta.-D-glucopyranosyluronic acid)cytosine, the nucleoside moiety of gougerotin. J. Org. Chem. 1970, 35, 231–236; Vorbrueggen, H. Adventures in Silicon-Organic Chemistry. Acc. Chem. Res. 1995, 28, 509–520; Epp, J. B.; Widlanski, T. S. Facile Preparation of Nucleoside-5'-carboxylic Acids. J. Org. Chem. 1999, 64, 293–295; Shute, R. E.; Rich, D. H. Synthesis and evaluation of novel activated mixed carbonate reagents for the introduction of the 2-(trimethylsilyl)ethoxycarbonyl (Teoc) protecting group. Synthesis 1987, 346–349; Fang, L.; Wan, M.; Pennacchio, M.; Pan, J. Evaluation of evaporative light-scattering detector for combinatorial library quantitation by reversed phase HPLC. J. Comb. Chem. 2000, 2, 254–257; Ward, Y. D.; Farina, V. Solid phase synthesis of aryl amines via palladium catalyzed amination of resin-bound aromatic bromides. Tetrahedron Lett. 1996, 37, 6993–6996; Forman, F. W.; Sucholeiki, I. Solid-Phase Synthesis of Biaryls via the Stille Reaction. J. Org. Chem. 1995, 60, 523–528; Plunkett, M. J.; Ellman, J. A. Solid-Phase Synthesis of Structurally Diverse 1,4-Benzodiazepine Derivatives Using the Stille Coupling Reaction. J. Am. Chem. Soc. 1995, 117, 3306–3307; Larhed, M.; Lindeberg, G.; Hallberg, A. Rapid microwave-assisted Suzuki coupling on solid-phase. Tetrahedron Lett. 1996, 37, 8219–8222.).

In general, this class shares a related hexopyranosyl cytosine moiety connected to a modified peptidic side-chain.

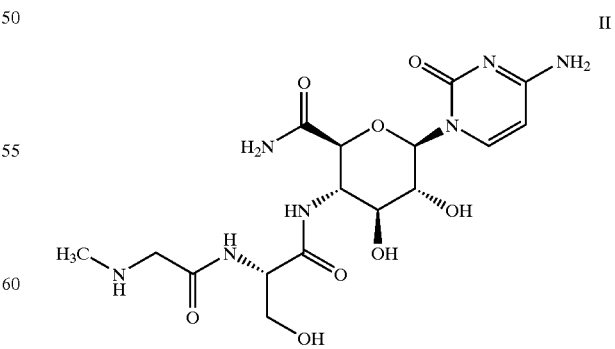

II

The present invention provides new compounds of this class having pharmaceutical activity together with methods for their synthesis and use.

BRIEF DESCRIPTION OF THE INVENTION

The present invention is directed to a compound of the formula (I), salts of this compound, pharmaceutical compositions and uses thereof: A compound of the formula (I):

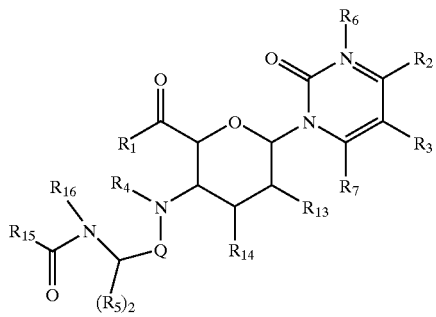

where $R_1$ is $\sim NR_8R_9$ or $\sim C(R_{10})_3$;

$R_2$, $R_3$ and $R_7$ each independently are $\sim NR_{11}R_{12}$, $\sim YZ$, alkyleno, substituted alkyleno, heteroalkyleno, substituted heteroalkyleno, aryleno, heteroaryleno, alkylenearyleno, arylenealkyleno, alkyleneheteroalkyleno, heteroyleno, halyleno, H radical or;

where $R_2$ and $R_3$ or $R_3$ and $R_7$, together form a ring including two atoms of the pyrimidine ring and having at least 1 additional ring atom;

each $R_5$ independently is alkyl, substituted alkyl, heteroalkyl, alkylenheteroyl, aryl, heteroaryl, $\sim(CH_2)_nN(R_{11}R_{12})$, $\sim(CH_2)_nG$ or H radical;

$R_6$ is an electron pair, alkyleno, heteroalkyleno, aryleno, heteroaryleno or H radical;

$R_4$, $R_{11}$, $R_{12}$, $R_{15}$ and $R_{16}$ each independently are alkyleno, heteroalkyleno, aryleno, heteroaryleno or H radical;

$R_8$ and $R_9$ each independently are alkyleno, heteroalkyleno, substituted heteroalkyleno, aryleno, heteroaryleno, H radical or together join to form an aminocyclic ring radical;

each $R_{10}$ independently is alkyleno, heteroalkyleno, aryleno, heteroaryleno, halyleno or H radical;

$R_{13}$ and $R_{14}$ each independently are alkyleno, heteroalkyleno, aryleno, heteroaryleno, halyleno, hydroxyleno or H radical;

Y is a heteroatom radical with Z a radical selected from the group comprising 1 or more heteroatoms or H, alkyleno, heteroalkyleno, aryleno, heteroaryleno, halyleno, combinations thereof and adapted to fill the valence of Y, said Y being singly or doubly bound to the pyrimidine ring radical;

Q is a member selected from the group of radicals comprising $\sim S(=O)\sim$, $\sim S(O)_2\sim$, $\sim C(=O)\sim$, $\sim C(=S)\sim$, $\sim CH_2\sim$, $\sim Y(O)\sim$ and $\sim C(Y)_n\sim$; where G is a cyclic alkyleno or cyclic heteroalkyleno substituent and n is an integer of at least 0; and with the proviso that;

when $R_2$ is $\sim NH_2$ and $R_9$ is $\sim H$, then;

$R_8$ is not an amino acid and;

the ratio of carbon atoms to nitrogen atoms of $R_5$ is greater than or equal to one and;

$R_{16}$ is H radical and;

$R_{15}$ does not comprise a

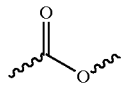

radical.

An additional aspect of the present invention is directed to methods of making the compounds according to structure (I), which may be practiced according to the following.

a) associating a compound according to structure III where A is a linker and G is a reaction-group, with a solid support for generating an intermediate compound associated with the solid support through said linker according to structure IIIa

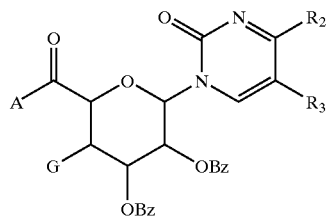

where ○ is the solid support;

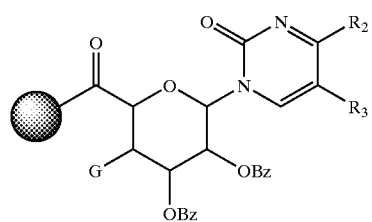

b) generating the intermediate compound IIIa associated with the solid support;

c) chemically manipulating said intermediate compound for generating the compound according to claim 1.

Definitions.

A preferred base utilized for alkylation is sodium hydride. Other suitable bases may also be utilized, however such bases must have sufficient base strength to remove the targeted proton from the starting material. While not wishing to be bound by theory, generally any base having a pKa about 10 pka units greater than the pKa of the targeted proton of the starting material may be used. More specifically, bases having a pKb greater than the pKb of sodium hydride may conveniently be selected. Such bases can be selected from compilations of base such as those given in Table 1, page 220 of March, J. *Advanced Organic Chemistry*, Wiley-Interscience, lohn Wiley & Sons, New York, 1985.

The alkylation reactions of the invention typically are conducted in DMF as the solvent. Other suitable solvents include DMSO, N-methyl pyrolidone and sulfolone.

Preferably, deamination is effected by use of deaminase enzymes. Particularly preferred is adenosine deaminase. Particularly suitable for use is Adenosine Deaminase Type II available from Sigma Chemical Company, St. Louis, Mo. Other deamination reagents may also be employed. The deamination reactions of the invention typically are conducted in a mixture of solvents containing an organic solvent and an aqueous buffer. Suitable for use as the organic solvent are DMSO, N-methyl pyrolidone and sulfolone. In preferred embodiments of the present invention deamination is achieved using DMSO as the organic solvent. Suitable for use as the aqueous buffer are buffers having a pH compatible to the pH range of use of the deaminase enzyme. Preferred are phophate buffers such as sodium phosphate and tris buffers.

In order to enrich one hydroxy derived product by elimination of any positional and/or structural analog products, a TIPS (trisopropylsiloxane) protecting group is utilized to protect one hydroxyl moieties of the sugar portions of the starting material to the exclusion of other hydroxyls. In the same manner, an exclusive product would be obtainable by use of a base stable, non-migratory hydroxyl protecting group. Such base stable, non-migratory protecting groups include but are not limited to tetrahydropyranyl (THP), 4-methoxytetrahydropyran4-yl (Mthp), 1-[(2chloro4-methyl)phenyl4-metboxypiperidin-4-yl (Cltmp), triphenylmethyl (trityl), mono-, di- and tri-methoxytrityl and other similar protecting groups.

Aliphatic and alicyclic groups suitable for use in the invention include but are not limited to saturated and unsaturated, straight and branch chain and alicyclic, substituted and unsubstituted alkyl, alkenyl and alkynyl groups including methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl and other higher carbon straight-chain alkyl groups, 2-methylpropyl, 2-methyl4-ethylbutyl, 2,4-diethylpropyl, 3-propylbutyl, 2,8-dibutyldecyl, 6,6-dimethyloctyl, 6-propyl-6-butyloctyl, 2-methylbutyl, 2-methylpentyl, 3-methylpentyl, 2-ethylhexyl and other branched-chain groups; allyl, crotyl, propargyl, 2-pentenyl and other unsaturated groups; and cyclohexane, cyclopentane, adamantane as well as other alicyclic groups. Preferred compounds are the $C_1$-$C_{20}$ alkyls, $C_1$-$C_{20}$ alkenes and $C_1$-$C_{20}$ alkynes. Most preferred are the $C_1$-$C_{20}$ straight chain alkyls.

Alkyl, alkenyl, and alkynyl groups according to the invention include but are not limited to substituted and unsubstituted straight chain, branch chain, and alicyclic hydrocarbons, including methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl and other higher carbon alkyl groups. Further examples include 2-methylpropyl, 2-methyl-4-ethylbutyl, 2-diethylpropyl, 3-propylbutyl, 2,8-dibutyldecyl, 6,6-dimethyloctyl, 6-propyl-6-butyloctyl, 2-methylbutyl, 2-methylpentyl, 3-methylpentyl, 2-ethylhexyl and other branched chain groups, allyl, crotyl, propargyl, 2-pentenyl and other unsaturated groups, cyclohexane, cyclopentane, adamantane as well as other alicyclic groups, 3-penten-2one, 3-methyl-2-butanol, 2-cyanooctyl, 3-methoxyheptanal, 3-nitrobutyl, 4-isopropaxydodecyl, azido-2-nitrodecyl, 5-mercaptononyl, 4-amino-1-pentenyl as well as other substituted groups.

Aryl groups according to the invention include but are not limited to substituted and unsubstituted aromatic hydrocarbyl groups such as phenyl and naphthyl groups. Aralkyl groups include but are not limited to groups having both aryl and alkyl functionality, such as benzyl groups.

As used herein, the term "alkyl" includes but is not limited to straight chain, branch chain, and alicyclic hydrocarbon groups. Alkyl groups of the present invention may be substituted. Representative alkyl substituents are disclosed in U.S. Pat. No. 5,212,295, at column 12, lines 41–50.

As used herein, the term "aralkyl" denotes alkyl groups, which bear aryl groups, for example, benzyl groups. The term "alkaryl" denotes aryl groups which bear alkyl groups, for example, methylphenyl groups. "Aryl" groups are aromatic cyclic compounds including but not limited to phenyl, naphthyl, anthracyl, phenanthryl, pyrenyl, and xylyl.

As used herein, the term O-alkylamino denotes a group of formula O-alkyl-NH~. The term O-alkylalkoxy denotes a group of formula —O-alkyl-O-silyl. The term O-alkylaminoalkyl denotes an O-alkylamino group wherein the amino moiety bears one or more additional alkyl groups.

As used herein, the term "heterocycloalkyl" denotes an alkyl ring system having one or more heteroatoms (i.e., non-carbon atoms). Preferred heterocycloalkyl groups include, for example, morpholino groups. As used herein, the term "heterocycloalkenyl" denotes a ring system having one or more double bonds, and one or more heteroatoms. Preferred heterocycloalkenyl groups include, for example, pyrrolidino groups.

Substituent groups according to the invention include but are not limited to halogen (Cl, Br, F), hydroxyl (OH), thiol (SH), keto (C=O), carboxy (COOH), ethers, thioethers, amidine (C(=NH)NR'R"), guanidine (NHC(=NH)NR'R"), glutamyl CH(NR'R")(C(=O)ORS), nitrate (ONO2), nitro ($NO_2$), nitrile (CN), trifluoromethyl ($CF_3$), trifluoromethoxy ($OCF_3$), O-alkyl, S-alkyl, NH-alkyl, N-dialkyl, O-aralkyl, S-aralkyl, NH-aralkyl, amino (NH2), azido ($N_3$), hydrazino ($NHNH_2$), hydroxylamino ($ONH_2$), sulfoxide (SO), sulfone ($SO_2$), sulfide (S—), disulfide (S—S), silyl, heterocyclic, alicyclic and carbocyclic. Preferred substituents include halogens, alcohols and ethers (OR,), thiols and thioethers ($SR_2$), amines (NR'R"), amidines [C(=NH)NR'R"], guanidines [NHC(=NH)NR'R"], aldehydes (CH=O), acids [C(=O)OH], esters [C(=O)OR], amides [C(=O)NR'R"] and glycine [$CH(NH_2)(C(=O)OH)$].

Further included are aliphatic and alicyclic groups (as defined above) that include substituent groups thereon. Such substituent groups include but are not necessarily limited to halogen (Cl, Br, F), hydroxyl (OH), thiol (SH), keto (C=O), carboxyl (COOH), nitrate (ONO2), nitro (NO2), nitroso (NO), nitrile (CN), trifluoromethyl (CF3), trifluoromethoxy (OCF3), O-alkyl, S-alkyl, NH-alkyl, N-dialkyl, O-aralkyl, S-aralkyl, NH-aralkyl, amino (NH2), azido (N3), hydrazino (NHNH2), hydroxylamino (ONH2), isocyanato (OCN), sulfoxide (SO), sulfone (SO2), sulfide (S—), disulfide (S—S), silyl, heterocyclic, alicyclic, carbocyclic, intercalators, reporter molecules, conjugates, polyamines, polyamides, polyethylene glycols, polyethers, groups that enhance the pharmacodynamic properties of oligonucleotides, and groups that enhance the pharmacokinetic properties of oligonucleotides. Such compounds include 3-penten-2-one, 3-methyl-2-butanol, 2-cyanooctyl, 3-methoxy, 4-heptanal, 3-nitrobutyl, 4-isopropoxydodecyl, 4-azido-2-nitrodecyl, 5-mercaptononyl, 4-amino-1-pentenyl as well as other substituted groups. These substituted groups can be introduced in a blocked or protected form and later de-blocked to the parent substituted compound. For example, use of the phthalimido group as a blocked form of an amino substitution is known by those of skill in the art and can be found within related publications and literature.

A number of substituent groups can be introduced into compounds of the invention in a protected (blocked) form and subsequently de-protected to form a final, desired compound. In general, protecting groups render chemical functionality unreactive to specific reaction conditions and can be appended to and removed from such functionality in a molecule without substantially damaging the remainder of the molecule. See, e.g., Green and Wuts, *Protective Groups in Organic Synthesis,* 2d edition, John Wiley & Sons, New York, 1991. For example, amino groups can be protected as phthalimido groups or as 9-fluorenylmethoxycarbonyl (FMOC) groups and carboxy groups can be protected as fluorenylmethyl groups. Representative hydroxyl protecting groups are described by Beaucage, et al., Tetrahedron 1992, 48, 2223.

One particularly preferred substituent group is CF3. Further particularly preferred substituent groups are phthalimido, piperazine and imidazole. As noted, use of the phthalimido group allows for introduction of a blocked amino functionality on the alkyl group. Utilizing phthalimido analogs prepared in accordance with this invention as intermediates synthesis is complete, the phthalimido group is removed yielding an amino functionality. Use of an imidazole moiety as a substituent group on the alkyl functionality introduces the suggested nucleic acid cleaving functionality, imidazole.

Nitrogen heterocycles suitable for use as the functional group include imidazole, pyrrole, pyrazole, indole, 1H-indazole, carboline, carbazole, phenothiazine, and phenoxazine groups. A more preferred group of nitrogen heterocycles includes imidazole, pyrrole, and carbazole groups. Imidazole and piperazine groups are especially preferred.

Purines and pyrimidines according to the invention include adenine, guanine, cytosine, uridine, and thymine, as well as other synthetic and natural nucleobases such as xanthine, hypoxanthine, 2-aminoadenine, 6-methyl and other alkyl derivatives of adenine and guanine, 2-propyl and other alkyl derivatives of adenine and guanine, 5-halo uracil and cytosine, 6-azo uracil, cytosine and thymine, 5-uracil (pseudo uracil), 4-thiouracil, 8-halo, amino, thiol, thioalkyl, hydroxyl and other 8-substituted adenines and guanines, 5-trifluoromethyl and other 5-substituted uracils and cytosines, 7-methylguanine. Further purines and pyrimidines include those disclosed in U.S. Pat. No. 3,687,808, those disclosed in the *Concise Encyclopedia Of Polymer Science And Engineering,* pages 858–859, Kroschwitz, J. I., ed. John Wiley & Sons, 1990, and those disclosed by Englisch, et al., *Angewandte Chemie, International Edition* 1991, 30, 613.

Solid supports according to the invention comprises controlled pore glass (CPG), oxalyl-controlled pore glass (see, e.g., Alul, et al., *Nucleic Acids Research* 1991, 19, 1527), aminopolyethyleneglycol derivatized support (see, e.g., Wright, et al., *Tetrahedron Letters* 1993, 34, 3373). A major class of solid-phase organic synthesis is based on crosslinked polystyrene resins beads as the solid support and is reviewed in *Chemical Reviews,* Guillier F., Orain D., Bradley M.; Chem. Rev. ;2000, 100, 2091–2157.

The term "alkoxy," as used herein, represents an alkyl group attached to the parent molecular group through an oxygen atom. Alkoxy groups are exemplified by methoxy, ethoxy, isopropoxy and the like.

The term "alkoxycarbonyl," as used herein, represents an ester group, i.e. an alkoxy group attached to the parent molecular group through a carbonyl group. Alkoxycarbonyl groups are exemplified by methnxycarbonyl, ethoxycarbonyl and the like.

The term "alkyl," as used herein, represents a monovalent group derived from a straight or branched chain saturated hydrocarbon by the removal of a single hydrogen atom. Alkyl groups are exemplified by methyl, ethyl, n-propyl and iso-propyl, n-butyl, sec-butyl, iso-butyl, tertbutyl neopentyl and the like.

The term "alkenyl," as used herein, represents a monovalent straight or branched chain of carbon atoms containing at least one carbon-carbon double bond derived from an alkene by the removal of one hydrogen atom. Alkenyl groups are exemplified by ethenyl, 1-propenyl, 2-propenyl, 2-methyl1-propenyl 1-butenyl, 2butenyl and the like.

The term "amino," as used herein, represents an $NH_2$ group.

The term "aminoalkyl," as user1 herein, represents an alkyl group substituted by an amino group. Aminoalkyl groups are exemplified by aminomethyl, 2-aminopropyl 3-aminopentyl and the like.

The term "aryl" as used herein, represents a mono- or bicyclic carbocyclic group having one or two aromatic rings. Aryl groups are exemplified by phenyl, naphthyl, 1,2dihydronaphthyl, 1,2,3,4-tetrahydronaphthyl, fluorenyl, indanyl, indenyl and the like.

The term "carboxy," as used herein, represents a $CO_2H$ group.

The term "carboxyalkyl," as used herein, represents an alkyl group substituted by a carboxy group.

The term "cyano," as used herein, represents a —(C≡N group.

The term "cycloalkyl," as used herein, represents a monovalent salurted cyclic hydrocarbon group. Cycloalkyl groups are exemplified by cyclopropyl, cyclobutyl, cyclopentyl, cyclohexyl, cycloheptyl, bicyclo[2.2.1]heptyl and the like.

The term "heteroaryl," as use herein, represents a ring containing one or two heteroatoms and sufficient double bonds to be considered aromatic. Heterocycles are exemplified by pyridine and pyrazine and may be optionally substituted with halo, alkoxy, phenyl or substituted phenyl.

The term "hydroxyl," as used herein, represents an —OH group.

The term "hydroxyalkyl," as used herein, represents an alkyl group substituted by one, two or three hydroxy groups, with the proviso that no more than one hydroxyl group may be attached to a single carbon atom of the alkyl group. Tetrahydroxyalkyl groups are exemplified by hydroxymethyl, dihydroxypropyl and the like.

The term "nitro," as used herein, represents an $—NO_2$ group.

The terms "N-protecting group" or "nitrogen protecting group" as used herein, represent those groups intended to protect an amino group against undesirable reactions during synthetic procedures. N-protecting groups comprise acyl groups such as formyl, acetyl, propionyl, pivaloyl, 1-butylacetyl 2-chlomacelyL 2-bromoacelyl, trichloroacetyl trichloroacetyl, phthalyl, o-nitrophenoxyacetyl, chlorobutyryl, benzoyl, 4-chlorobenzoyl, 4-bromobenzoyl, 4-nitrobenzoyl and chiral auxiliaries such as protected or unprotected D, L or D, L-amino acids such as alanine, leucine, phenylalanine and the like; sulfonyl groups such as benzenesulfonyl, p-toluenesulionyl and the like; carbamate forming groups such as benzyloxycarbonyl, p-chlorobenzyloxycarbonyl p-methoxybenzyloxycarbonyl, p-nitrobcnzyloxycarbonyl, 2-nitrobcnzyloxycarbonyl, p-bromobenzyloxycarbonyl, 3,4-dimethoxybenzyloxycarbonyl, 3,5-dimelhexylbenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, N,N-dimethyl-3,5 dimethoxybenzyloxycarbonyl, benzylhdryloxycarbonyl, t-butyloxycarbonyl, diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxy carbonyl, fluorenyl- 9-methoxycarbonyl, cyclopentyloxycarbonyl, adamantyloxycarbonyl, cyclohexyloxycarbonyl, phenylthiocarbonyl and the like; arylalkyl groups such as benzyl, triphenylmethyl, benzyloxymethyl and the like and silyl groups such as trimethylsilyl and the like. Preferred N-protecting groups are formyl, acetyl, benzoyl, pivaloyl, t-blnylacetyl, phenyLsulfonyl, benzyl, t-butyloxycarbonyl (Boc) and benzyloxycarbonyl (Cbz).

The term "N-protected amino," as used herein, represents an amino group to which is attached an N-protecting or nitrogen-protecting group.

The term "O-protected carboxyl" as used herein, represents an ester or amide group intended to protect a carboxyl group against undesirable reactions during synthetic procedures. Additionally, a carboxyl protecting group can be used as a prodrug whereby the carboxy protecting group can be readily cleaved in vivo, for example, by enzymatic hydrolysis, to release the biologically-active parent compound. Such carboxyl protecting groups are well-known to those skilled in the art, having been extensively used in the protection of carboxyl groups in the penicillin and cephalosporin fields as described in U.S. Pat. Nos. 3,840,556 and 3,719,667. Representative carboxyl protecting groups are $C_1$–$C_8$ loweralkyl (e.g., methyl ethyl or t-butyl and the like); arylalkyl such as phenethyl or benzyl and substituted derivatives thereof such as alkoxybenzyl or nitrobenzyl groups and the like; arylalkenyl such as phenylethenyl and the like; aryl and substituted derivatives thereof such as 5-indanyl and the like; dialkylaminoalkyl such as dimethylaminoethyl and the like); alkanoylalkylalkyl groups such as acetoxymethyl, butyryloxymethyl, valeryloxymethyl, isobutyryloxymethyl, isovaleryloxymethyl, 1-methyl-1-(propionyloxy)-1-ethyl, pivaloyloxymethyl, propionyloxymethyl and the like; cycloalkanoyloxyalkyl groups such as cyclopropylcarbonyloxymethyl, cyclobutylcarbonyloxymethyl, cyclopentylcarbonyloxymethyl, cyclohexylcarbonyloxymethyl and the like; aroyloxyalkyl such as benzoyloxymethyL benzoyloxyethyl and the like; arylalkylcarbonyloxyalkyl such as benzylcarbonyloxymethyl, 2-benzylcarbonyloxyethyl and the like; alkoxycarbonylalkyl or cycloalkyloxycarbonylalkyl such as methoxycarbonylmethyl, cyclohexyloxycarbonyl methy 1, 1-methoxycarbonyl-1-ethyl and the like; alkoxycarbonyloxyalkyl or cycloalkyloxycarbonyloxyalkyl such as methoxycarbonyloxymethyl, t-butyloxycarbonyloxymethyl, 1-ethoxycarbonyloxy-1-ethyl, 1-cyclohexyloxycarbonyloxy-1-ethyl and the like, aryloxycarbonyloxyallyl such as 2-(phenoxycarbonyloxyalkyl, 2,5-indanyloxycarbonyloxy)ethyl and the like; alkoxyalkylcarbonyloxyalkyl such as 2-(1-methoxy-2-methylpropan-2oyloxy)ethyl and like; arylalkyloxycarbonyloxyalkyl such as 2-(benzyloxycarbonyloxy)ethyl and the like; arylaLkenyloxyearbonyloxyalkyl such as 2-(3-phenylpropen-2yloxycarbonyloxy)ethyl and the like; aLkoxycarbonyla~ninoalkyl such as t-butyloxycarbonylaminomethyl and the like; alkylaminocarbonylaminnalkyl such ac methylaminocarbonylaminomethyl and the like; alkanoylaminoalkyl such as acetylaminomethyl and the like; heterocycliccarbonyloxyalkyl such as 4-methylpiperazinylcarbonyloxymethyl and the like; dialkylaminocarbonylalkyl such as dimethylaminocarbonylmethyl, diethylaminocarbonyl-ethyl and the like; (5-(lower alkyl)-2-oxo-1,3-dioxolen-4-yl)alkyl and such as (5-s-butyl-2-oxo-1,3-dioxolen-4-yl)methyl and the like; and (5-phenyl-2-oxo-1,3-dioxolen-4-yl)alkyl such as (5-phenyl-2-oxo-1,3-dioxolen-4-yl)methyl and the like.

The term "parenterally," as used herein, refers to modes of administration which include intravenous, intramuscular, intraperitoneal subcutaneous and intraarticular injection and infusion.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable. Preferred oral formulations are those in which oligomeric compounds of the invention are administered in conjunction with one or more penetration enhancers surfactants and chelators. Preferred surfactants include fatty acids and/or esters or salts thereof, bile acids and/or salts thereof. Preferred bile acids/salts include chenodeoxycholic acid (CDCA) and ursodeoxychenodeoxycholic acid (UDCA), cholic acid, dehydrocholic acid, deoxycholic acid, glucholic acid, glycholic acid, glycodeoxycholic acid, taurocholic acid, taurodeoxycholic acid, sodium tauro-24,25-dihydro-fusidate, sodium glycodihydrofusidate. Preferred fatty acids include arachidonic acid, undecanoic acid, oleic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcamitine, an acylcholine, or a monoglyceride, a diglyceride or a pharmaceutically acceptable salt thereof (e.g. sodium). Also preferred are combinations of penetration enhancers, for example, fatty acids/salts in combination with bile acids/salts. A particularly preferred combination is the sodium salt of lauric acid, capric acid and UDCA. Further penetration enhancers include polyoxyethylene-9-lauryl ether, polyoxyethylene-20-cetyl ether. Oligomeric compounds of the invention may be delivered orally in granular form including sprayed dried particles, or complexed to form micro or nanoparticles. Oligonucleotide complexing agents include poly-amino acids; polyimines; polyacrylates; polyalkylacrylates, polyoxethanes, polyalkylcyanoacrylates; cationized gelatins, albumins, starches, acrylates, polyethyleneglycols (PEG) and starches; polyalkylcyanoacrylates; DEAE-derivatized polyimines, pollulans, celluloses and starches. Particularly preferred complexing agents include chitosan, N-trimethylchitosan, poly-L-lysine, polyhistidine, polyomithine, polyspermines, protamine, polyvinylpyridine, polythiodiethylamino-methylethylene P(TDAE), polyaminostyrene (e.g. p-amino), poly(methylcyanoacrylate), poly (ethylcyanoacrylate), poly(butylcyanoacrylate), poly (isobutylcyanoacrylate), poly(isohexylcynaoacrylate), DEAE-methacrylate, DEAE-hexylacrylate, DEAE-acrylamide, DEAE-albumin and DEAE-dextran, polymethylacrylate, polyhexylacrylate, poly(D,L-lactic acid), poly(DL-lactic-co-glycolic acid (PLGA), alginate, and polyethyleneglycol (PEG). Oral formulations for oligonucleotides and their preparation are described in detail in U.S. applications Ser. Nos. 08/886,829 (filed Jul. 1, 1997), 09/108,673 (filed Jul. 1, 1998), 09/256,515 (filed Feb. 23, 1999), 09/082,624 (filed May 21, 1998) and 09/315,298 (filed May 20, 1999) each of which is incorporated herein by reference in their entirety.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient (s). In general the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, gel capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

In one embodiment of the present invention the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product. The preparation of such compositions and formulations is generally known to those skilled in the pharmaceutical and formulation arts and may be applied to the formulation of the compositions of the present invention.

The compositions of the present invention may be prepared and formulated as emulsions. Emulsions are typically heterogenous systems of one liquid dispersed in another in the form of droplets usually exceeding 0.1 μm in diameter. (Idson, in Pharmaceutical Dosage Forms, Lieberman, Rieger and Banker (Eds.), 1988, Marcel Dekker, Inc., New York, N.Y., volume 1, p. 199; Rosoff, in Pharmaceutical Dosage Forms, Lieberman, Rieger and Banker (Eds.), 1988, Marcel Dekker, Inc., New York, N.Y., Volume 1, p. 245; Block in Pharmaceutical Dosage Forms, Lieberman, Rieger and Banker (Eds.), 1988, Marcel Dekker, Inc., New York, N.Y., volume 2, p. 335; Higuchi et al., in Remington's Pharmaceutical Sciences, Mack Publishing Co., Easton, Pa., 1985, p. 301). Emulsions are often biphasic systems comprising of two immiscible liquid phases intimately mixed and dispersed with each other. In general, emulsions may be either water-in-oil (w/o) or of the oil-in-water (o/w) variety. When an aqueous phase is finely divided into and dispersed as minute droplets into a bulk oily phase the resulting composition is called a water-in-oil (w/o) emulsion. Alternatively, when an oily phase is finely divided into and dispersed as minute droplets into a bulk aqueous phase the resulting composition is called an oil-in-water (o/w) emulsion. Emulsions may contain additional components in addition to the dispersed phases and the active drug which may be present as a solution in either the aqueous phase, oily phase or itself as a separate phase. Pharmaceutical excipients such as emulsifiers, stabilizers, dyes, and anti-oxidants may also be present in emulsions as needed. Pharmaceutical emulsions may also be multiple emulsions that are comprised of more than two phases such as, for example, in the case of oil-in-water-in-oil (o/w/o) and water-in-oil-in-water (w/o/w) emulsions. Such complex formulations often provide certain advantages that simple binary emulsions do not. Multiple emulsions in which individual oil droplets of an o/w emulsion enclose small water droplets constitute a w/o/w emulsion. Likewise a system of oil droplets enclosed in globules of water stabilized in an oily continuous provides an o/w/o emulsion.

Emulsions are characterized by little or no thermodynamic stability. Often, the dispersed or discontinuous phase of the emulsion is well dispersed into the external or continuous phase and maintained in this form through the means of emulsifiers or the viscosity of the formulation. Either of the phases of the emulsion may be a semisolid or a solid, as is the case of emulsion-style ointment bases and creams. Other means of stabilizing emulsions entail the use of emulsifiers that may be incorporated into either phase of the emulsion. Emulsifiers may broadly be classified into four categories: synthetic surfactants, naturally occurring emulsifiers, absorption bases, and finely dispersed solids (Idson, in Pharmaceutical Dosage Forms, Lieberman, Rieger and Banker (Eds.), 1988, Marcel Dekker, Inc., New York, N.Y., volume 1, p. 199).

Synthetic surfactants, also known as surface active agents, have found wide applicability in the formulation of emulsions and have been reviewed in the literature (Rieger, in Pharmaceutical Dosage Forms, Lieberman, Rieger and Banker (Eds.), 1988, Marcel Dekker, Inc., New York, N.Y., volume 1, p. 285; Idson, in Pharmaceutical Dosage Forms, Lieberman, Rieger and Banker (Eds.), Marcel Dekker, Inc., New York, N.Y., 1988, volume 1, p. 199). Surfactants are typically amphiphilic and comprise a hydrophilic and a hydrophobic portion. The ratio of the hydrophilic to the hydrophobic nature of the surfactant has been termed the hydrophile/lipophile balance (HLB) and is a valuable tool in categorizing and selecting surfactants in the preparation of formulations. Surfactants may be classified into different classes based on the nature of the hydrophilic group: nonionic, anionic, cationic and amphoteric (Rieger, in Pharmaceutical Dosage Forms, Lieberman, Rieger and Banker (Eds.), 1988, Marcel Dekker, Inc., New York, N.Y., volume 1, p. 285).

Naturally occurring emulsifiers used in emulsion formulations include lanolin, beeswax, phosphatides, lecithin and acacia. Absorption bases possess hydrophilic properties such that they can soak up water to form w/o emulsions yet retain their semisolid consistencies, such as anhydrous lanolin and hydrophilic petrolatum. Finely divided solids have also been used as good emulsifiers especially in combination with surfactants and in viscous preparations. These include polar inorganic solids, such as heavy metal hydroxides, nonswelling clays such as bentonite, attapulgite, hectorite, kaolin, montmorillonite, colloidal aluminum silicate and colloidal magnesium aluminum silicate, pigments and nonpolar solids such as carbon or glyceryl tristearate.

A large variety of non-emulsifying materials are also included in emulsion formulations and contribute to the properties of emulsions. These include fats, oils, waxes, fatty acids, fatty alcohols, fatty esters, humectants, hydrophilic colloids, preservatives and antioxidants (Block, in Pharmaceutical Dosage Forms, Lieberman, Rieger and Banker (Eds.), 1988, Marcel Dekker, Inc., New York, N.Y., volume 1, p. 335; Idson, in Pharmaceutical Dosage Forms, Lieberman, Rieger and Banker (Eds.), 1988, Marcel Dekker, Inc., New York, N.Y., volume 1, p. 199).

Hydrophilic colloids or hydrocolloids include naturally occurring gums and synthetic polymers such as polysaccharides (for example, acacia, agar, alginic acid, carrageenan, guar gum, karaya gum, and tragacanth), cellulose derivatives (for example, carboxymethylcellulose and carboxypropylcellulose), and synthetic polymers (for example, carbomers, cellulose ethers, and carboxyvinyl polymers). These disperse or swell in water to form colloidal solutions that stabilize emulsions by forming strong interfacial films around the dispersed-phase droplets and by increasing the viscosity of the external phase.

Since emulsions often contain a number of ingredients such as carbohydrates, proteins, sterols and phosphatides that may readily support the growth of microbes, these formulations often incorporate preservatives. Commonly used preservatives included in emulsion formulations include methyl paraben, propyl paraben, quaternary ammonium salts, benzalkonium chloride, esters of p-hydroxybenzoic acid, and boric acid. Antioxidants are also commonly added to emulsion formulations to prevent deterioration of the formulation. Antioxidants used may be free radical scavengers such as tocopherols, alkyl gallates, butylated hydroxyanisole, butylated hydroxytoluene, or reducing agents such as ascorbic acid and sodium metabisulfite, and antioxidant synergists such as citric acid, tartaric acid, and lecithin.

The application of emulsion formulations via dermatological, oral and parenteral routes and methods for their manufacture have been reviewed in the literature (Idson, in Pharmaceutical Dosage Forms, Lieberman, Rieger and Banker (Eds.), 1988, Marcel Dekker, Inc., New York, N.Y., volume 1, p. 199). Emulsion formulations for oral delivery have been very widely used because of reasons of ease of formulation, efficacy from an absorption and bioavailability standpoint. (Rosoff, in Pharmaceutical Dosage Forms, Lieberman, Rieger and Banker (Eds.), 1988, Marcel Dekker, Inc., New York, N.Y., volume 1, p. 245; Idson, in Pharmaceutical Dosage Forms, Lieberman, Rieger and Banker (Eds.), 1988, Marcel Dekker, Inc., New York, N.Y., volume 1, p. 199). Mineral-oil base laxatives, oil-soluble vitamins and high fat nutritive preparations are among the materials that have commonly been administered orally as o/w emulsions.

Surfactants used in the preparation of microemulsions include, but are not limited to, ionic surfactants, non-ionic surfactants, Brij 96, polyoxyethylene oleyl ethers, polyglycerol fatty acid esters, tetraglycerol monolaurate (ML310), tetraglycerol monooleate (MO310), hexaglycerol monooleate (PO310), hexaglycerol pentaoleate (PO500), decaglycerol monocaprate (MCA750), decaglycerol monooleate (MO750), decaglycerol sequioleate (SO750), decaglycerol decaoleate (DAO750), alone or in combination with cosurfactants. The cosurfactant, usually a short-chain alcohol such as ethanol, 1-propanol, and 1-butanol, serves to increase the interfacial fluidity by penetrating into the surfactant film and consequently creating a disordered film because of the void space generated among surfactant molecules. Microemulsions may, however, be prepared without the use of cosurfactants and alcohol-free self-emulsifying microemulsion systems are known in the art. The aqueous phase may typically be, but is not limited to, water, an aqueous solution of the drug, glycerol, PEG300, PEG400, polyglycerols, propylene glycols, and derivatives of ethylene glycol. The oil phase may include, but is not limited to, materials such as Captex 300, Captex 355, Capmul MCM, fatty acid esters, medium chain (C8–C12) mono, di, and tri-glycerides, polyoxyethylated glyceryl fatty acid esters, fatty alcohols, polyglycolized glycerides, saturated polyglycolized C8–C10 glycerides, vegetable oils and silicone oil.

Microemulsions are particularly of interest from the standpoint of drug solubilization and the enhanced absorption of drugs. Lipid based microemulsions (both o/w and w/o) have been proposed to enhance the oral bioavailability of drugs, including peptides (Constantinides et al., Pharmaceutical Research, 1994, 11, 1385–1390; Ritschel, Meth. Find. Exp. Clin. Pharmacol., 1993, 13, 205). Microemulsions afford advantages of improved drug solubilization, protection of drug from enzymatic hydrolysis, possible enhancement of drug absorption due to surfactant-induced alterations in membrane fluidity and permeability, ease of preparation, ease of oral administration over solid dosage forms, improved clinical potency, and decreased toxicity (Constantinides et al., Pharmaceutical Research, 1994, 11, 1385; Ho et al., J. Pharm. Sci., 1996, 85, 138–143). Often microemulsions may form spontaneously when their components are brought together at ambient temperature. This may be particularly advantageous when formulating thermolabile drugs, peptides or oligonucleotides. Microemulsions have also been effective in the transdermal delivery of active components in both cosmetic and pharmaceutical applications. It is expected that the microemulsion compositions and formulations of the present invention will facilitate the increased systemic absorption of oligonucleotides and nucleic acids from the gastrointestinal tract, as well as improve the local cellular uptake of oligonucleotides and nucleic acids within the gastrointestinal tract, vagina, buccal cavity and other areas of administration.

Microemulsions of the present invention may also contain additional components and additives such as sorbitan monostearate (Grill 3), Labrasol, and penetration enhancers to improve the properties of the formulation and to enhance the absorption of the oligomeric compounds and nucleic acids of the present invention. Penetration enhancers used in the microemulsions of the present invention may be classified as belonging to one of five broad categories—surfactants, fatty acids, bile salts, chelating agents, and non-chelating non-surfactants (Lee et al., Critical Reviews in Therapeutic Drug Carrier Systems, 1991, p. 92). Each of these classes has been discussed above.

There are many organized surfactant structures besides microemulsions that have been studied and used for the formulation of drugs. These include monolayers, micelles, bilayers and vesicles. Vesicles, such as liposomes, have attracted great interest because of their specificity and the duration of action they offer from the standpoint of drug delivery. As used in the present invention, the term "liposome" means a vesicle composed of amphiphilic lipids arranged in a spherical bilayer or bilayers.

Liposomes are unilamellar or multilamellar vesicles which have a membrane formed from a lipophilic material and an aqueous interior. The aqueous portion contains the composition to be delivered. Cationic liposomes possess the advantage of being able to fuse to the cell wall. Non-cationic liposomes, although not able to fuse as efficiently with the cell wall, are taken up by macrophages in vivo. In order to cross intact mammalian skin, lipid vesicles must pass through a series of fine pores, each with a diameter less than 50 nm, under the influence of a suitable transdermal gradient. Therefore, it is desirable to use a liposome which is highly deformable and able to pass through such fine pores.

Further advantages of liposomes include; liposomes obtained from natural phospholipids are biocompatible and biodegradable; liposomes can incorporate a wide range of water and lipid soluble drugs; liposomes can protect encapsulated drugs in their internal compartments from metabolism and degradation (Rosoff, in Pharmaceutical Dosage Forms, Lieberman, Rieger and Banker (Eds.), 1988, Marcel Dekker, Inc., New York, N.Y., volume 1, p. 245). Important considerations in the preparation of liposome formulations are the lipid surface charge, vesicle size and the aqueous volume of the liposomes.

Liposomes are useful for the transfer and delivery of active ingredients to the site of action. Because the liposomal membrane is structurally similar to biological membranes, when liposomes are applied to a tissue, the liposomes start to merge with the cellular membranes. As the merging of the liposome and cell progresses, the liposomal contents are emptied into the cell where the active agent may act.

Liposomal formulations have been the focus of extensive investigation as the mode of delivery for many drugs. There is growing evidence that for topical administration, liposomes present several advantages over other formulations. Such advantages include reduced side-effects related to high systemic absorption of the administered drug, increased accumulation of the administered drug at the desired target, and the ability to administer a wide variety of drugs, both hydrophilic and hydrophobic, into the skin.

Several reports have detailed the ability of liposomes to deliver agents including high-molecular weight DNA into the skin. Compounds including analgesics, antibodies, hormones and high-molecular weight DNAs have been administered to the skin. The majority of applications resulted in the targeting of the upper epidermis.

Liposomes fall into two broad classes. Cationic liposomes are positively charged liposomes which interact with the negatively charged DNA molecules to form a stable complex. The positively charged DNA/liposome complex binds to the negatively charged cell surface and is internalized in an endosome. Due to the acidic pH within the endosome, the liposomes are ruptured, releasing their contents into the cell cytoplasm (Wang et al., Biochem. Biophys. Res. Commun., 1987, 147, 980–985).

Liposomes which are pH-sensitive or negatively-charged, entrap DNA rather than complex with it. Since both the DNA and the lipid are similarly charged, repulsion rather than complex formation occurs. Nevertheless, some DNA is entrapped within the aqueous interior of these liposomes. pH-sensitive liposomes have been used to deliver DNA encoding the thymidine kinase gene to cell monolayers in culture. Expression of the exogenous gene was detected in the target cells (Zhou et al., Journal of Controlled Release, 1992, 19, 269–274).

One major type of liposomal composition includes phospholipids other than naturally-derived phosphatidylcholine. Neutral liposome compositions, for example, can be formed from dimyristoyl phosphatidylcholine (DMPC) or dipalmitoyl phosphatidylcholine (DPPC). Anionic liposome compositions generally are formed from dimyristoyl phosphatidylglycerol, while anionic fusogenic liposomes are formed primarily from dioleoyl phosphatidylethanolamine (DOPE). Another type of liposomal composition is formed from phosphatidylcholine (PC) such as, for example, soybean PC, and egg PC. Another type is formed from mixtures of phospholipid and/or phosphatidylcholine and/or cholesterol.

Several studies have assessed the topical delivery of liposomal drug formulations to the skin. Application of liposomes containing interferon to guinea pig skin resulted in a reduction of skin herpes sores while delivery of interferon via other means (e.g. as a solution or as an emulsion) were ineffective (Weiner et al., Journal of Drug Targeting, 1992, 2, 405–410). Further, an additional study tested the efficacy of interferon administered as part of a liposomal formulation to the administration of interferon using an aqueous system, and concluded that the liposomal formulation was superior to aqueous administration (du Plessis et al., Antiviral Research, 1992, 18, 259–265).

Non-ionic liposomal systems have also been examined to determine their utility in the delivery of drugs to the skin, in particular systems comprising non-ionic surfactant and cholesterol. Non-ionic liposomal formulations comprising Novasome™ I (glyceryl dilaurate/cholesterol/polyoxyethylene-10-stearyl ether) and Novasome™ II (glyceryl distearate/cholesterol/polyoxyethylene-10-stearyl ether) were used to deliver cyclosporin-A into the dermis of mouse skin. Results indicated that such non-ionic liposomal systems were effective in facilitating the deposition of cyclosporin-A into different layers of the skin (Hu et al. S.T.P.Pharma. Sci., 1994, 4, 6, 466).

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome (A) comprises one or more glycolipids, such as monosialoganglioside $G_{M1}$, or (B) is derivatized with one or more hydrophilic polymers, such as a polyethylene glycol (PEG) moiety. While not wishing to be bound by any particular theory, it is thought in the art that, at least for sterically stabilized liposomes containing gangliosides, sphingomyelin, or PEG-derivatized lipids, the enhanced circulation half-life of these sterically stabilized liposomes derives from a reduced uptake into cells of the reticuloendothelial system (RES) (Allen et al., FEBS Letters, 1987, 223, 42; Wu et al., Cancer Research, 1993, 53, 3765). Various liposomes comprising one or more glycolipids are known in the art. Papahadjopoulos et al. (Ann. N.Y. Acad. Sci., 1987, 507, 64) reported the ability of monosialoganglioside $G_{M1}$, galactocerebroside sulfate and phosphatidylinositol to improve blood half-lives of liposomes. These findings were expounded upon by Gabizon et al. (Proc. Natl. Acad. Sci. U.S.A., 1988, 85, 6949). U.S. Pat. No. 4,837,028 and WO 88/04924, both to Allen et al., disclose liposomes comprising (1) sphingomyelin and (2) the ganglioside $G_{M1}$ or a galactocerebroside sulfate ester. U.S. Pat. No. 5,543,152 (Webb et al.) discloses liposomes comprising sphingomyelin. Liposomes comprising 1,2-sn-dimyristoylphosphatidylcholine are disclosed in WO 97/13499 (Lim et al.).

Many liposomes comprising lipids derivatized with one or more hydrophilic polymers, and methods of preparation thereof, are known in the art. Sunamoto et al. (Bull. Chem. Soc. Jpn., 1980, 53, 2778) described liposomes comprising a nonionic detergent, $2C_{12}15G$, that contains a PEG moiety. Illum et al. (FEBS Lett., 1984, 167, 79) noted that hydrophilic coating of polystyrene particles with polymeric glycols results in significantly enhanced blood half-lives. Synthetic phospholipids modified by the attachment of carboxylic groups of polyalkylene glycols (e.g., PEG) are described by Sears (U.S. Pat. Nos. 4,426,330 and 4,534,899). Klibanov et al. (FEBS Lett., 1990, 268, 235) described experiments demonstrating that liposomes comprising phosphatidylethanolamine (PE) derivatized with PEG or PEG stearate have significant increases in blood circulation half-lives. Blume et al. (Biochimica et Biophysica Acta, 1990, 1029, 91) extended such observations to other PEG-derivatized phospholipids, e.g., DSPE-PEG, formed from the combination of distearoylphosphatidylethanolamine (DSPE) and PEG. Liposomes having covalently bound PEG moieties on their external surface are described in European Patent No. EP 0 445 131 B1 and WO 90/04384 to Fisher. Liposome compositions containing 1–20 mole percent of PE derivatized with PEG, and methods of use thereof, are described by Woodle et al. (U.S. Pat. Nos. 5,013,556 and 5,356,633) and Martin et al. (U.S. Pat. No. 5,213,804 and European Patent No. EP 0 496 813 B1). Liposomes comprising a number of other lipid-polymer conjugates are disclosed in WO 91/05545 and U.S. Pat. No. 5,225,212 (both to Martin et al.) and in WO 94/20073 (Zalipsky et al.) Liposomes comprising PEG-modified ceramide lipids are described in WO 96/10391 (Choi et al.). U.S. Pat. No. 5,540,935 (Miyazaki et al.) and U.S. Pat. No. 5,556,948 (Tagawa et al.) describe PEG-containing liposomes that can be further derivatized with functional moieties on their surfaces.

A limited number of liposomes comprising nucleic acids are known in the art. WO 96/40062 to Thierry et al. discloses methods for encapsulating high molecular weight nucleic acids in liposomes. U.S. Pat. No. 5,264,221 to Tagawa et al. discloses protein-bonded liposomes and asserts that the contents of such liposomes may include an antisense RNA. U.S. Pat. No. 5,665,710 to Rahman et al. describes certain methods of encapsulating oligodeoxynucleotides in liposomes. WO 97/04787 to Love et al. discloses liposomes comprising antisense oligonucleotides targeted to the raf gene.

Transfersomes are yet another type of liposomes, and are highly deformable lipid aggregates which are attractive candidates for drug delivery vehicles. Transfersomes may be described as lipid droplets which are so highly deformable that they are easily able to penetrate through pores which are smaller than the droplet. Transfersomes are adaptable to the environment in which they are used, e.g. they are self-optimizing (adaptive to the shape of pores in the skin), self-repairing, frequently reach their targets without fragmenting, and often self-loading. To make transfersomes it is possible to add surface edge-activators, usually surfactants, to a standard liposomal composition. Transfersomes have been used to deliver serum albumin to the skin. The transfersome-mediated delivery of serum albumin has been shown to be as effective as subcutaneous injection of a solution containing serum albumin.

Surfactants find wide application in formulations such as emulsions (including microemulsions) and liposomes. The most common way of classifying and ranking the properties of the many different types of surfactants, both natural and synthetic, is by the use of the hydrophile/lipophile balance (HLB). The nature of the hydrophilic group (also known as the "head") provides the most useful means for categorizing the different surfactants used in formulations (Rieger, in Pharmaceutical Dosage Forms, Marcel Dekker, Inc., New York, N.Y., 1988, p. 285).

If the surfactant molecule is not ionized, it is classified as a nonionic surfactant. Nonionic surfactants find wide application in pharmaceutical and cosmetic products and are usable over a wide range of pH values. In general their HLB values range from 2 to about 18 depending on their structure. Nonionic surfactants include nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. The polyoxyethylene surfactants are the most popular members of the nonionic surfactant class.

If the surfactant molecule carries a negative charge when it is dissolved or dispersed in water, the surfactant is classified as anionic. Anionic surfactants include carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates. The most important members of the anionic surfactant class are the alkyl sulfates and the soaps.

If the surfactant molecule carries a positive charge when it is dissolved or dispersed in water, the surfactant is classified as cationic. Cationic surfactants include quaternary ammonium salts and ethoxylated amines. The quaternary ammonium salts are the most used members of this class.

If the surfactant molecule has the ability to carry either a positive or negative charge, the surfactant is classified as amphoteric. Amphoteric surfactants include acrylic acid derivatives, substituted alkylamides, N-alkylbetaines and phosphatides. The use of surfactants in drug products, formulations and in emulsions has been reviewed (Rieger, in Pharmaceutical Dosage Forms, Marcel Dekker, Inc., New York, N.Y., 1988, p. 285).

In one embodiment, the present invention employs various penetration enhancers to effect the efficient delivery of nucleic acids, particularly oligomeric compounds, to the skin of animals. Most drugs are present in solution in both ionized and nonionized forms. However, usually only lipid soluble or lipophilic drugs readily cross cell membranes. It has been discovered that even non-lipophilic drugs may cross cell membranes if the membrane to be crossed is treated with a penetration enhancer. In addition to aiding the diffusion of non-lipophilic drugs across cell membranes, penetration enhancers also enhance the permeability of lipophilic drugs. Penetration enhancers may be classified as belonging to one of five broad categories, i.e., surfactants, fatty acids, bile salts, chelating agents, and non-chelating non-surfactants (Lee et al., Critical Reviews in Therapeutic Drug Carrier Systems, 1991, p.92). Each of the above mentioned classes of penetration enhancers are described below in greater detail.

In connection with the present invention, surfactants (or "surface-active agents") are chemical entities which, when dissolved in an aqueous solution, reduce the surface tension of the solution or the interfacial tension between the aqueous solution and another liquid, with the result that absorption of oligonucleotides through the mucosa is enhanced. In addition to bile salts and fatty acids, these penetration enhancers include, for example, sodium lauryl sulfate, polyoxyethylene-9-lauryl ether and polyoxyethylene-20-cetyl ether) (Lee et al., Critical Reviews in Therapeutic Drug Carrier Systems, 1991, p.92); and perfluorochemical emulsions, such as FC-43. Takahashi et al., J. Pharm. Pharmacol., 1988, 40, 252).

Various fatty acids and their derivatives which act as penetration enhancers include, for example, oleic acid, lauric acid, capric acid (n-decanoic acid), myristic acid, palmitic acid, stearic acid, linoleic acid, linolenic acid, dicaprate, tricaprate, monoolein (1-monooleoyl-rac-glycerol), dilaurin, caprylic acid, arachidonic acid, glycerol 1-monocaprate, 1-dodecylazacycloheptan-2-one, acylcarnitines, acylcholines, $C_{1-10}$ alkyl esters thereof (e.g., methyl, isopropyl and t-butyl), and mono- and di-glycerides thereof (i.e., oleate, laurate, caprate, myristate, palmitate, stearate, linoleate, etc.) (Lee et al., Critical Reviews in Therapeutic Drug Carrier Systems, 1991, p.92; Muranishi, Critical Reviews in Therapeutic Drug Carrier Systems, 1990, 7, 1–33; El Hariri et al., J. Pharm. Pharmacol., 1992, 44, 651–654).

The physiological role of bile includes the facilitation of dispersion and absorption of lipids and fat-soluble vitamins (Brunton, Chapter 38 in: Goodman & Gilman's The Pharmacological Basis of Therapeutics, 9th Ed., Hardman et al. Eds., McGraw-Hill, New York, 1996, pp. 934–935). Various natural bile salts, and their synthetic derivatives, act as penetration enhancers. Thus the term "bile salts" includes any of the naturally occurring components of bile as well as any of their synthetic derivatives. The bile salts of the invention include, for example, cholic acid (or its pharmaceutically acceptable sodium salt, sodium cholate), dehydrocholic acid (sodium dehydrocholate), deoxycholic acid (sodium deoxycholate), glucholic acid (sodium glucholate), glycholic acid (sodium glycocholate), glycodeoxycholic acid (sodium glycodeoxycholate), taurocholic acid (sodium taurocholate), taurodeoxycholic acid (sodium taurodeoxycholate), chenodeoxycholic acid (sodium chenodeoxycholate), ursodeoxycholic acid (UDCA), sodium tauro-24,25-dihydro-fusidate (STDHF), sodium glycodihydrofusidate and polyoxyethylene-9-lauryl ether (POE) (Lee et al., Critical Reviews in Therapeutic Drug Carrier Systems, 1991, page 92; Swinyard, Chapter 39 In: Remington's Pharmaceutical Sciences, 18th Ed., Gennaro, ed., Mack Publishing Co., Easton, Pa., 1990, pages 782–783; Muranishi, Critical Reviews in Therapeutic Drug Carrier Systems, 1990, 7, 1–33; Yamamoto et al., J. Pharm. Exp. Ther., 1992, 263, 25; Yamashita et al., J. Pharm. Sci., 1990, 79, 579–583).

The term "pharmaceutically acceptable ester," as used herein, represents esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl group preferably has no more than 6 carbon atoms. Examples of particular esters includes formates, acetates, propionates, butyrates, acrylates and ethylsuccinates.

The term "pharmaceutically acceptable salt," as use herein, represents those salts which are, within the scope of sound medical judgement, suitable for use in contact with the tissues of humans and lower animals without undue toxicity, irritation, allergic response and the like and are commensurate with a reasonable benefit/risk ratio.

Pharmaceutically acceptable salts are well-known in the art. The salts can be prepared in situ during the final isolation and purification of the compounds of the invention or separately by reacting the free base group with a suitable organic acid. Representative acid addition salts include acetate, adipate, algioate, ascorbate, aspartate, benzenesulfonate, benzoate, bisulfate, borate, butyrate, camphorate, camphersulfonate, citrate, cyclopentanepropionate, digluconate, dodecylsulfate, ethanesulfonate, fumarate, glucosephsphonate, glycophosphonate, hydrobromide, hydrochloride, hydroiodide, 2-hydroxylhanesulfonate, lactobionate, lactate, laurate, laurylsulfonate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts and the like. Representative alkali or alkaline earth metal salts include sodium, lithium, potassium, calcium, magnesium and the like, as well as nontoxic ammonium, quaternary ammonium, and amine cations, including, but not limited to ammonium, tetramethylammonium, tetraethylammonium, methylamine, dimelhylamine, trimclhylamine, triclLylaminc, elhylamine and the like.

Asymmetric or chiral centers may exist in the compounds of the present invention. The present invention contemplates the various stereoisomers and mixtures thereof. Individual streoisomers of compounds of the present invention are prepared synthetically from commercially available starting materials which contain asymmetric or chiral centers or by preparation of mixtures of enantiomeric compounds followed by resolution well-known to those of ordinary skill in the art. These methods of resolution are exemplified by (1) attachment of a racemic mixture of enantiomers, designated to a chiral auxiliary, separation of the resulting diastereomers by recrystallization or chromatography and liberation of the optically pure product from the auxiliary or (2) direct separation of the mixture of optical enantiomers on chiral chromatographic columns. Enantiomers are designated herein by the symbols "R" or "S," depending on the configuration of substituents around the chiral carbon atom.

The reactions of the synthetic methods claimed herein are carried out in suitable solvents which may be readily selected by one of skill in the art of organic synthesis, said suitable solvents generally being any solvent which is substantially nonreactive with the starting materials (reactants), the intermediates, or products at the temperatures at which the reactions are carried out, i.e., temperatures which may range from the solvent's freezing temperature to the solvent's boiling temperature. A given reaction may be carried out in one solvent or a mixture of more than one solvent. Depending on the particular reaction step, suitable solvents for a particular reaction step may be selected.

As used herein, suitable aprotic solvents include, by way of example and without limitation, ether solvents and hydrocarbon solvents. Suitable ether solvents include tetrahydrofuran, diethyl ether, diethoxymethane, ethylene glycol dimethyl ether, ethylene glycol diethyl ether, diethylene glycol dimethyl ether, diethylene glycol diethyl ether, triethylene glycol dimethyl ether, or t-butyl methyl ether. Suitable hydrocarbon solvents include: butane, pentane, hexane, heptane, octane, nonane, decane, cyclohexane, cycloheptane, methylcyclohexane; as well as aryl hydrocarbon solvents.

As used herein, suitable acetate solvents include methyl, ethyl, propyl and iso-propyl acetate.

As used herein, suitable halogenated solvents to chlorobutane, methylene chloride, chloroform, dichloroethane, and carbon tetrachloride.

As used herein, suitable aryl solvents include toluene, benzene, o-xylene, m-xylene and p-xylene.

As used herein the term "acylating agent" or "strongly electrophilic acylating agent" refers to any agent which can acylate a primary amine. Acylating agent generally refers to agents of formula $R_1C(=O)R_2$ which can selectively acylate one primary amine in the presence of a second primary amine. Examples of acylating agents include $R_2$ as an alkoxy or phenoxy group and $R_1$ as a $C_1$–$C_4$ haloalkyl group, such as $CF_3$, $CF_2CF_3$, $CF_2CF_2CF_3$, $CF_2Cl$, $CF_2Br$, $Cl_3$, $CBr_3$, or $CH_2F$. "Strongly electrophilic acylating agent" generally refers to agents which can nonselectively acylate two primary amines in one molecule, for example anhydrides of formula, $R_1(CO)O(CO)R_1$, or $R_1$ substituted acid halides, ea. $R_1C(=O)Cl$, but may also include acylating agents of formula $R_1C(=O)R_2$ depending on the reaction conditions as determined by one of skill in the art to synthesize a compound of formula (II). Examples of strongly electrophilic acylating agents are where R1 is a C1–C3 haloalkyl, such as $CF_3$, $CF_2CF_3$, $CF_2CF_2CF_3$, $CF_2Cl$, $CF_2Br$, $CCl_3$, $CBr_3$, or $CH_2F$.

As used herein, the term "reducing agent" refers to any agent which can effect the reduction of an imine to an amine without effecting a chemical change on any other substitutents on the diamine substrate. Examples of reducing agents include hydrogen metal catalysts, chemical reducing agents, and catalytic transfer hydrogenation. Examples of hydrogen metal catalysts include, but are not limited to, Pd/C, Pt/C, Rh/C, and Raney-Nickel. Examples of chemical reducing agents include, but are not limited to, sodium triacetoxy borohydride, sodium borohydride, pyridine/borane, lithium aluminum hydride, lithium borohydride, sodium cyanoborohydride, and sodium amalgam.

As used herein, the term "hydrolyzing agent" means a reagent capable of generating sufficient hydroxide ion in solution to remove the acyl group from a compound of formula (III). Examples of suitable hydrolyzing agents include but are not limited to sodium hydroxide in methanol, potassium hydroxide in isopropanol and potassium hydroxide in n-butanol.

As used herein, the term "cyclizing agent" means a reagent that can effect the formation of a cyclic urea from the diamine. Examples of suitable cyclizing agents include but are not limited to phosgene, diphosgene, triphosgene, 1,1'-carbonyl diumidazole, phenyl chloroformate, 4-nitro-phenyl chloroformate, phenyl tetrazoylformate, oxalyl chloride, N,N'-disuccinimidyl carbonate, trichloromethyl chloroformate, $C_1$–$C_4$ dialkyl carbonate, ethylene carbonate, vinylene carbonate, and 2(S),3 pyridinediyl carbonate.

As used herein, "cycloalkyl" is intended to include saturated ring groups, including mono-, bi- or poly-cyclic ring systems, such as cyclopropyl, cyclobutyl, cyclopentyl, cyclohexyl, cycloheptyl, adamantyl and cyclooctyl.

As used herein, "carbocycle" or "carbocyclic" is intended to mean any stable 3- to 7-membered monocyclic or bicyclic or 7- to 14-membered bicyclic or tricyclic or an up to 26-membered polycyclic carbon ring, any of which may be saturated, partially unsaturated, or aromatic. Examples of such carbocyles include, but are not limited to, cyclopropyl, cyclopentyl, cyclohexyl, phenyl, biphenyl, naphthyl, indanyl, adamantyl, or tetrahydronaphthyl (tetralin).

As used herein "haloalkyl" is intended to include both branched and straight-chain saturated aliphatic hydrocarbon groups having the specified number of carbon atoms, substituted with 1 or more halogen. For example, C1–C4 haloalkyl includes, but is not limited to, $CF_3$, $CF_2CF_3$, $CF_2CF_2CF_3$, $CF_2CF_2CF_2CF_3$, $CF_2Cl$, $CF_2Br$, $CCl_3$, $CBr_3$, $CH_2F$, $CH_2CF_3$, and the like.

As used herein "alkoxy" represents an alkyl group of indicated number of carbon atoms attached through an oxygen bridge. For example C1–C4 alkoxy includes methoxy, ethoxy, propoxy and butoxy. As used herein "cycloalkoxy" represents a cycloalkyl group of indicated number of carbon atoms attached through an oxygen bridge. For example C3–C6 cycloalkoxy includes cyclopropyloxy, cyclobutyloxy, cyclopentyloxy, and cyclohexyloxy.

As used herein "alkylcarbonyl" is intended to include an alkyl group of an indicated number of carbon atoms attached through a carbonyl group to the residue of the compound at the designated location. For example C1–C4 alkylcarbonyl includes methylcarbonyl, ethylcarbonyl, propylcarbonyl and butylcarbonyl.

As used herein "alkylcarbonyloxy" is intended to include an alkyl group of an indicated number of carbon atoms attached to a carbonyl group, where the carbonyl group is attached through an oxygen atom to the residue of the compound at the designated location.

As used herein "alkylcarbonylamino" is intended to include an alkyl group of an indicated number of carbon atoms attached to a carbonyl group, where the carbonyl group is attached through an amino group to the residue of the compound at the designated location.

The pharmaceutically acceptable salts of the present invention can be synthesized from the parent compound which contain a basic or acidic moiety by conventional chemical methods. Generally, pharmaceutically acceptable salts of the compounds of the invention can be prepared by reacting the free acid or base forms of these compounds with a stoichiometric amount of the appropriate base or acid, respectively, in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ea., Mack Publishing Company, Easton, Pa., 1985, p. 1418, the disclosure of which is hereby incorporated by reference.

It is understood that where the processes of the invention describe the use of a suitable acid to form an acid addition salt, one of skill in the art of synthesis can use an inorganic or an organic acid which could also render a pharmaceutically acceptable salt. In addition to the acids listed above for pharmaceutically acceptable salts the following acids are examples of suitable acids for the formation of an acid addition salt: phthalic acid, salicylic acid, isophthalic acid, and malonic acid.

As used herein, suitable recrystallization solvents include those in which the product will dissolve when heated and crystallize when cooled. Examples include, but are not limited to alkanes, ethers, esters (acetates), alcohols, aryls, halogenated alkanes, organic acids and water.

When any variable (for example, $R_{10}$, etc.) occurs more than one time in any constituent or formula for a compound, its definition on each occurrence is independent of its definition at every other occurrence. Thus, for example, if a group is shown to be substituted with 3 $R_4$, then said group may optionally be substituted with up to three $R_3$ and $R_3$ at each occurrence is selected independently from the defined list of possible $R_3$. Also, combinations of substitutents and/or variables are permissible only if such combinations result in stable compounds. By stable compound or stable structure it is meant herein a compound that is sufficiently robust to survive isolation to a useful degree of purity from a reaction mixture. Similarly, by way of example, for the group $C(R_2)$, each of the two $R_2$ substitutents on C is independently selected from the defined list of possible $R_2$.

The compounds herein described may have asymmetric centers. All chiral, diastereomeric, and racemic forms are included in the present invention. It will be appreciated that certain compounds of the present invention contain an asymmetrically substituted carbon atom, and may be isolated in optically active or racemic forms. It is well known in the art how to prepare optically active forms, such as by resolution of racemic forms or by synthesis, from optically active starting materials. All chiral, diastereomeric, racemic forms and all geometric isomeric forms of a structure are intended, unless the specific stereochemistry or isomer form is specifically indicated.

Combinations of substitutents and/or variables are permissible only if such combinations result in stable compounds. By stable compound or stable structure it is meant herein a compound that is sufficiently robust to survive isolation to a useful degree of purity from a reaction mixture.

The term "substituted", as used herein, means that one or more hydrogen on the designated atom is replaced with a selection from the indicated group, provided that the designated atom's normal valency is not exceeded, and that the substitution results in a stable compound.

DETAILED DESCRIPTION OF PREFERRED EMBODIMENTS

One aspect of the present invention is directed to a compound of the formula (I):

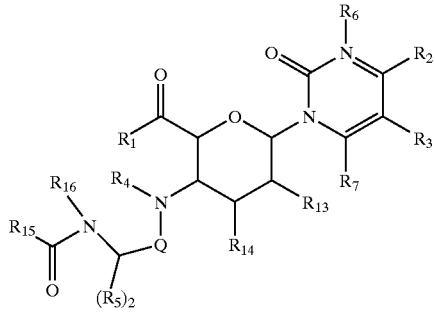

where $R_1$ is $NR_8R_9$ or $C(R_{10})_3$;

$R_2$, $R_3$ and $R_7$ each independently are $NR_{11}R_{12}$, YZ, alkyl, heteroalkyl, aryl, heteroaryl alkylenearyl, arylenealkyl, alkyleneheteroalkyl, heteroyl, halyl, H or;

where $R_2$ and $R_3$ or $R_3$ and $R_7$, together form a ring sharing two atoms of the pyrimidine ring and having at least 1 additional ring atom;

each $R_5$ independently is alkyl, heteroalkyl, alkylenheteroyl, aryl, heteroaryl, ~$(CH_2)_nN(R_{11}R_{12})$, ~$(CH_2)_nG$ or H;

$R_6$ is an electron pair, alkyl, heteroalkyl, aryl, heteroaryl or H;

$R_4$, $R_8$, $R_9$, $R_{11}$, $R_{12}$, $R_{15}$ and $R_{16}$ each independently are alkyl, heteroalkyl, aryl, heteroaryl or H;

each $R_{10}$ independently is alkyl, heteroalkyl, aryl, heteroaryl, halyl or H;

$R_{13}$ and $R_{14}$ each independently are alkyl, heteroalkyl, aryl, heteroaryl, halyl, hydroxyl or H;

Y is a heteroatom with Z selected from the group comprising 1 or more heteroatoms or H, alkyl, heteroalkyl, aryl, heteroaryl, halyl, combinations thereof and adapted to fill the valence of Y, said Y being singly or doubly bound to the pyrimidine ring;

Q is a member selected from the group comprising ~S(=O)~, ~S(O)$_2$~, ~C(=O)~, ~C(=S)~, ~CH$_2$~, ~Y(O)~ and ~C(Y)$_n$~; where Y is a heteroatom, G is a cyclic alkyl or cyclic heteroalkyl substituent and n is an integer of at least 0; and with the proviso that;

when $R_2$ is $NH_2$ and at least one of $R_8$ and $R_9$ is H, then; neither of $R_8$ nor $R_9$ is an amino acid and;

the ratio of carbon atoms to nitrogen atoms of $R_5$ must be greater than or equal to one, $R_{16}$ must be H, $R_{15}$ does not comprise an ester-bond and $R_{15}$ is not comprised of glycine or sarcosine.

A further embodiment of the present invention is directed to a pharmaceutical composition comprising: a compound of formula (I) and pharmaceutically acceptable salts thereof, associated with a pharmaceutically acceptable carrier, diluent, prodrug or lubricant;

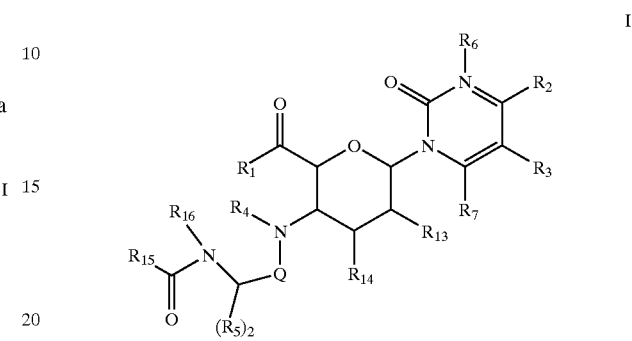

where $R_1$ is $NR_8R_9$ or $C(R_{10})_3$;

$R_2$, $R_3$ and $R_7$ each independently are $NR_{11}R_{12}$, YZ, alkyl, heteroalkyl, aryl, heteroaryl alkylenearyl, arylenealkyl, alkyleneheteroalkyl, heteroyl, halyl, H or;

where $R_2$ and $R_3$ or $R_3$ and $R_7$, together form a ring sharing two atoms of the pyrimidine ring and having at least 1 additional ring atom;

each $R_5$ independently is alkyl, heteroalkyl, alkylenheteroyl, aryl, heteroaryl, ~$(CH_2)_nN(R_{11}R_{12})$, ~$(CH_2)_nG$ or H;

$R_6$ is an electron pair, alkyl, heteroalkyl, aryl, heteroaryl or H;

$R_4$, $R_8$, $R_9$, $R_{11}$, $R_{12}$, $R_{15}$ and $R_{16}$ each independently are alkyl, heteroalkyl, aryl, heteroaryl or H;

each $R_{10}$ independently is alkyl, heteroalkyl, aryl, heteroaryl, halyl or H;

$R_{13}$ and $R_{14}$ each independently are alkyl, heteroalkyl, aryl, heteroaryl, halyl, hydroxyl or H;

Y is a heteroatom with Z selected from the group comprising 1 or more heteroatoms or H, alkyl, heteroalkyl, aryl, heteroaryl, halyl, combinations thereof and adapted to fill the valence of Y, said Y being singly or doubly bound to the pyrimidine ring;

Q is a member selected from the group comprising ~S(=O)~, ~S(O)$_2$~, ~C(=O)~, ~C(=S)~, ~CH$_2$~, ~Y(O)~ and ~C(Y)$_n$~; where Y is a heteroatom, G is a cyclic alkyl or cyclic heteroalkyl substituent and n is an integer of at least 0; and with the proviso that;

when $R_2$ is $NH_2$ and at least one of $R_8$ and $R_9$ is H, then; neither of $R_8$ nor $R_9$ is an amino acid and;

the ratio of carbon atoms to nitrogen atoms of $R_5$ must be greater than or equal to one, $R_{16}$ must be H, $R_{15}$ does not comprise an ester-bond and $R_{15}$ is not comprised of glycine or sarcosine.

An additional aspect of the present invention is directed to a method of making compounds of formula (I)

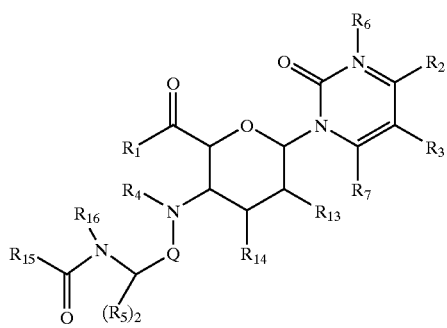

I

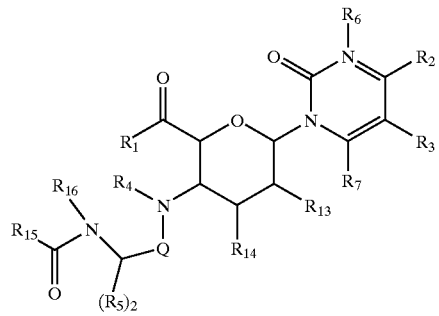

I comprising:

a) associating a compound according to structure III where A is a linker and G is a reaction-group, with a solid support for generating an intermediate compound associated with the solid support through said linker according to structure IIIa

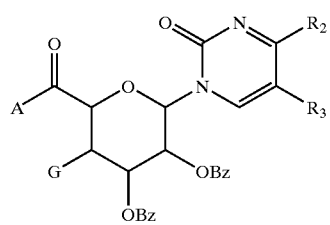

III where ⊙ is the solid support;

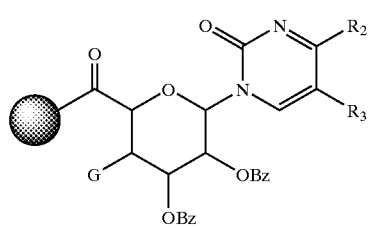

IIIa b) generating the intermediate compound IIIa associated with the solid support;

c) chemically manipulating said intermediate compound for generating the compound according to structure I; and d) obtaining the compound according to structure I.

A yet further embodiment of the present invention is directed to a method of using a compound or a pharmaceutically acceptable salt thereof comprising a compound of the formula (I):

i) obtaining a compound according to structure I;

ii) associating said compound with a pharmaceutical composition suitable for a pharmaceutical use iii) administering said pharmaceutical composition in a pharmaceutically acceptable manner.

These and other aspects of the present invention are explained in the following examples and through the subsequent Claims.

EXAMPLES AND SYNTHETIC METHODS

Scheme 1.[a] Sugar Precursor Synthesis

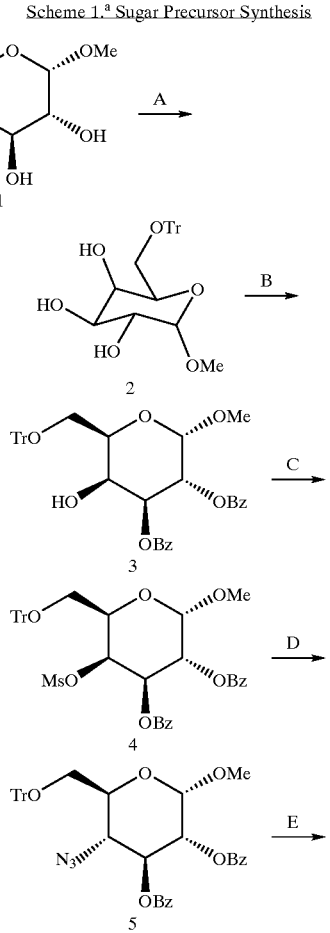

-continued

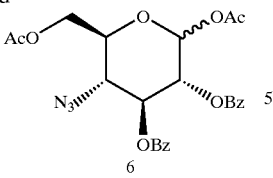

[a]A) tritylchloride, pyridine, DCM; B) 2.1 equiv. BzCl, pyridine; C) mesylchloride, pyridine; D) NaN$_3$, 80° C., HMPA; E) AcCl, Ac2O, H2SO4 (cat.)

We treated α-methyl galactopyranoside 1 with trityl chloride in the presence of pyridine in dichloromethane to effect selective tritylation at the 6-OH group, giving compound 2. Sugar 2 was then treated with 2.1 equivalents of benzoyl chloride in cold pyridine to benzoylate exclusively at the two free equatorial hydroxy groups to give protected sugar 3. The remaining axial hydroxy group of compound 3 was functionalized as a mesylate to give compound 4, which was subsequently treated with sodium azide to effect an Sn2 displacement giving glucopyranose 5. Treatment of fully functionalized sugar 5 under acetolysis conditions gave glycosyl donor 6, which was fully characterized by NMR.

Scheme 2.[a] Synthesis of Solid Phase Precursors.

6 →[A]

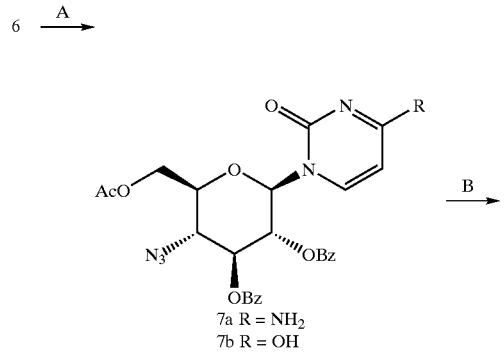

7a R = NH$_2$
7b R = OH

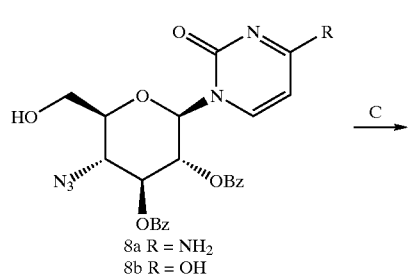

8a R = NH$_2$
8b R = OH

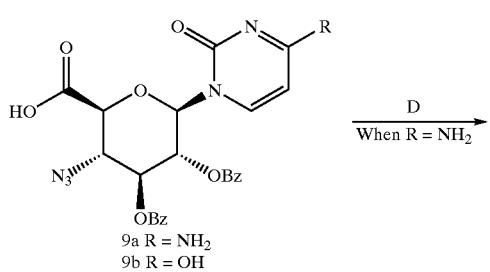

9a R = NH$_2$
9b R = OH

-continued

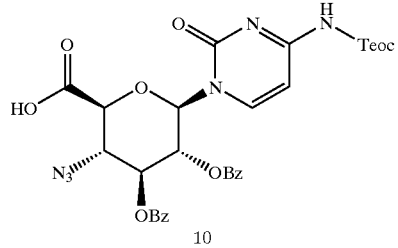

10

[a]A) BSA, SnCl$_4$, DME, N-Acetylcytidine or BSA, TMSOTf, CH$_3$CN, Uracil; B) Et$_3$N, MeOH, C) TEMPO, BIAB, CH$_3$CN/H$_2$O; D) Teoc-OSu, DIPEA, DMF, 60° C., 2 days Coupling of N-acetyl cytidine or uracil with donor 6 under modified Vorbrueggen conditions (Scheme 2) gave pyranosyl nucleoside 7a and 7b, respectively, which were treated individually with triethylamine in methanol to saponify the remaining acetate protecting groups and afford compounds 8a and 8b. Oxidation of the free primary hydroxy group of intermediates 8a and 8b using TEMPO radical gave carboxylic acid 9a and 9b. Finally, protection of the exocyclic N-4 of compound 9a as a trimethylsilylethyl-carbamate (Teoc) gave fully protected 10.

Scheme 3.[a]
Synthesis of Gougerotin and Analogs.

9b or 10 →[A]

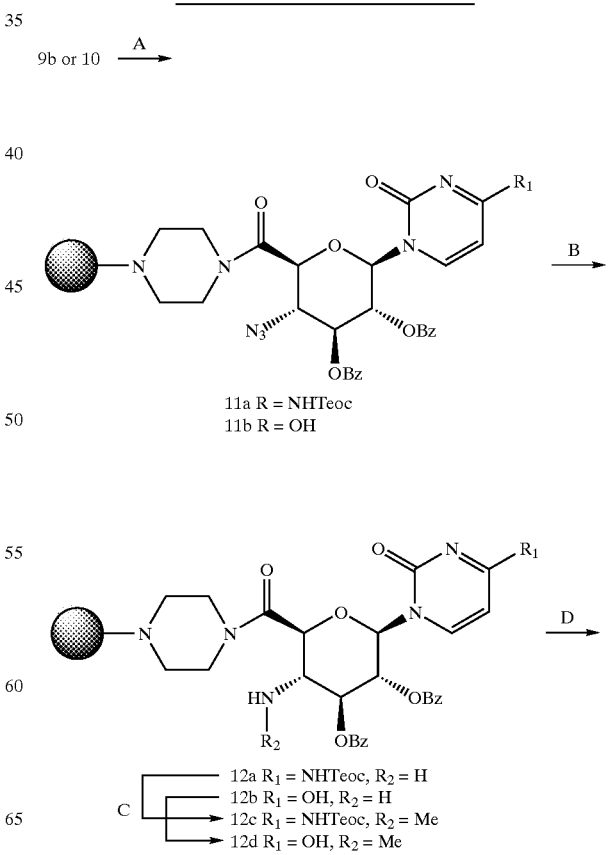

11a R = NHTeoc
11b R = OH

12a R$_1$ = NHTeoc, R$_2$ = H
12b R$_1$ = OH, R$_2$ = H
12c R$_1$ = NHTeoc, R$_2$ = Me
12d R$_1$ = OH, R$_2$ = Me

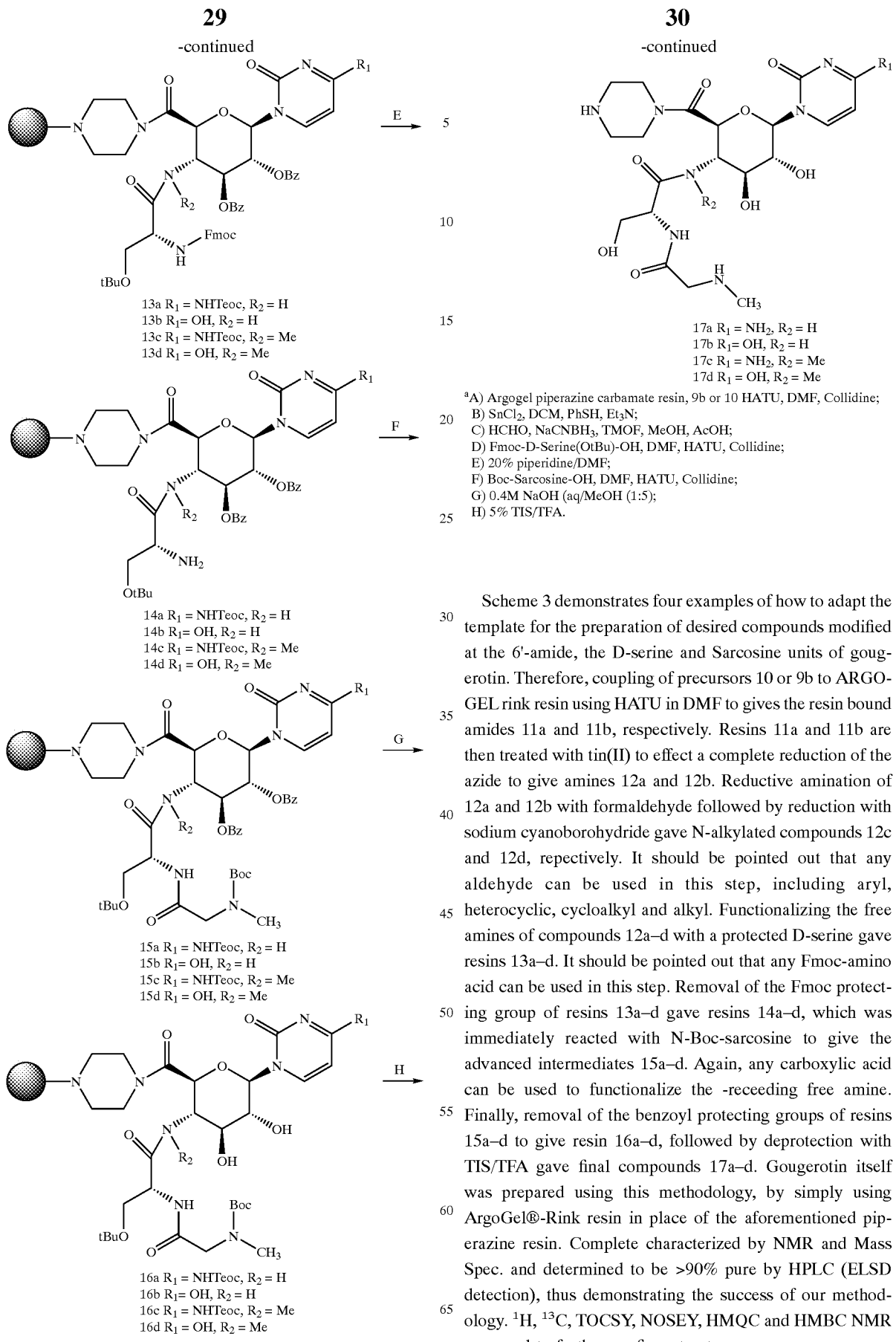

a) A) Argogel piperazine carbamate resin, 9b or 10 HATU, DMF, Collidine;
B) SnCl$_2$, DCM, PhSH, Et$_3$N;
C) HCHO, NaCNBH$_3$, TMOF, MeOH, AcOH;
D) Fmoc-D-Serine(OtBu)-OH, DMF, HATU, Collidine;
E) 20% piperidine/DMF;
F) Boc-Sarcosine-OH, DMF, HATU, Collidine;
G) 0.4M NaOH (aq/MeOH (1:5);
H) 5% TIS/TFA.

Scheme 3 demonstrates four examples of how to adapt the template for the preparation of desired compounds modified at the 6'-amide, the D-serine and Sarcosine units of gougerotin. Therefore, coupling of precursors 10 or 9b to ARGOGEL rink resin using HATU in DMF to gives the resin bound amides 11a and 11b, respectively. Resins 11a and 11b are then treated with tin(II) to effect a complete reduction of the azide to give amines 12a and 12b. Reductive amination of 12a and 12b with formaldehyde followed by reduction with sodium cyanoborohydride gave N-alkylated compounds 12c and 12d, repectively. It should be pointed out that any aldehyde can be used in this step, including aryl, heterocyclic, cycloalkyl and alkyl. Functionalizing the free amines of compounds 12a–d with a protected D-serine gave resins 13a–d. It should be pointed out that any Fmoc-amino acid can be used in this step. Removal of the Fmoc protecting group of resins 13a–d gave resins 14a–d, which was immediately reacted with N-Boc-sarcosine to give the advanced intermediates 15a–d. Again, any carboxylic acid can be used to functionalize the -receeding free amine. Finally, removal of the benzoyl protecting groups of resins 15a–d to give resin 16a–d, followed by deprotection with TIS/TFA gave final compounds 17a–d. Gougerotin itself was prepared using this methodology, by simply using ArgoGel®-Rink resin in place of the aforementioned piperazine resin. Complete characterized by NMR and Mass Spec. and determined to be >90% pure by HPLC (ELSD detection), thus demonstrating the success of our methodology. $^1$H, $^{13}$C, TOCSY, NOSEY, HMQC and HMBC NMR was used to further confirm structures.

31

Scheme 4.ᵃ Synthesis of Gougerotin N-4 Analogs

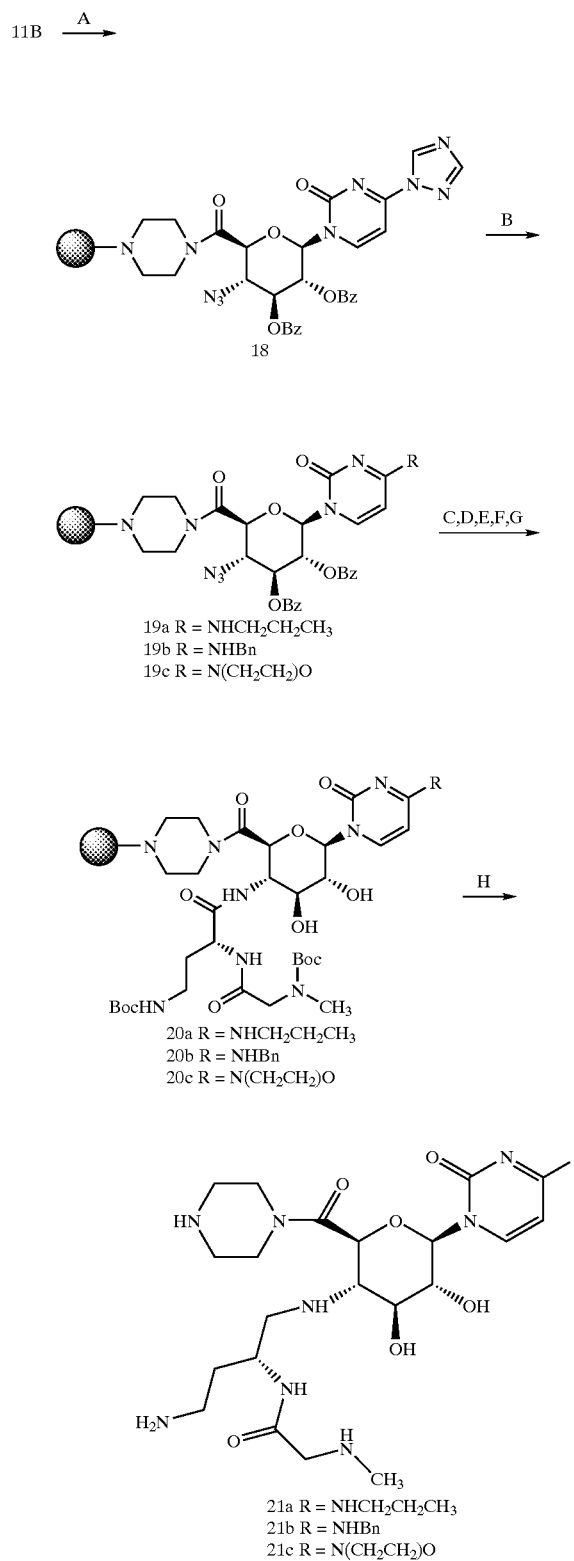

ᵃA) 1,2,4-triazole, POCl₃, Et₃N, CH₃CN; B) CH₃CH₂CH₂NH₂, 1,4-dioxane; C) SnCl₂, DCM, PhSH, Et₃N; D) N₄-Boc-N₂-FMoc-D-diaminobutanoic acid, DMF, HATU, Collidine; E) 20% piperidine/DMF; F) Boc-Sarcosine-OH, DMF, HATU, Collidine; G) 0.4M NaOH (aq)/MeOH (1:5); H) 5% TIS/TFA.

32

The common intermediate 11b is then used to prepare analogs substituted on N-4. Therefore, treatment of 11b with a premixed mixture of phosphorous oxychloride, triethylamine and 1,2,4-triazole in acetonitrile gives triazole intermediate 18. Displacement with n-propylamine gives the N-4 substituted intermediate 19a. The benzylamine (19b) and morpholine (19c) analogs were prepared in a similar manner as demonstrated in this step, any primary or secondary amine will work. Treatment of compound 19a–c using identical conditions as was used for the conversion of compounds 12a–d, gives 20a–c, and, after deprotection, compounds 21a–c.

Scheme 5.ᵃ Synthesis of Gougerotin N-5 Analogs

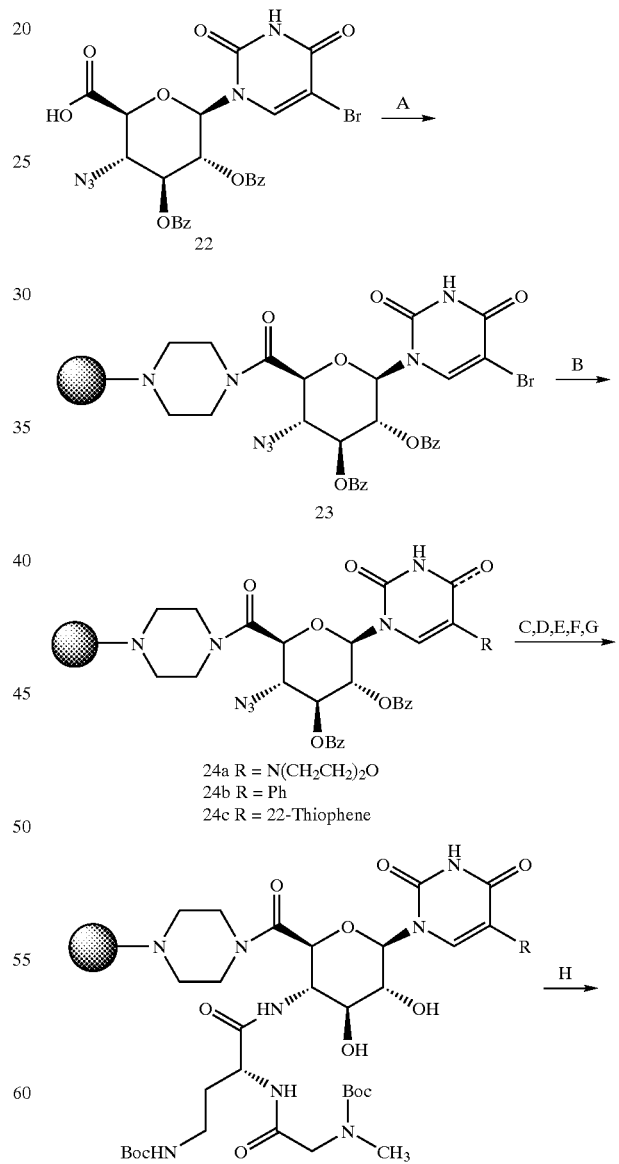

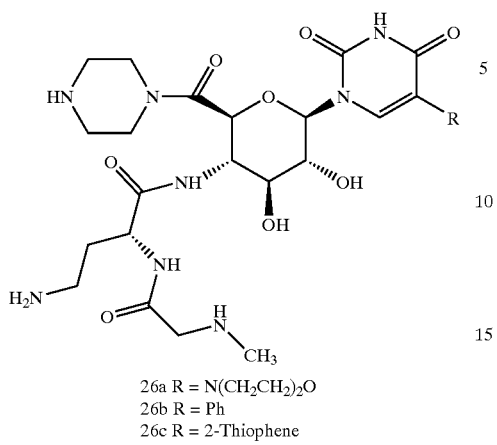

26a R = N(CH₂CH₂)₂O
26b R = Ph
26c R = 2-Thiophene

[a] A) Argogel piperazine carbamate resin, HATU, DMF, Collidine; B) suzuki, stille, buchwald; C) SnCl₂, DCM, PhSH, Et₃N; D) N₄-Boc-N₂-FMoc-D-diaminobutanoic acid, DMF, HATU, Collidine; E) 20% piperidine/DMF; F) Boc-Sarcosine-OH, DMF, HATU, Collidine; G) 0.4M NaOH (aq)/MeOH (1:5); H) 5%TIS/TFA.

By substituting 5-bromouracil N-acetylcytidine in our general synthetic scheme we can obtain precursor 22 (Scheme 5). Coupling of this precursor to ArgoGel® piperazine carbamate resin will give us the key intermediate 23. From this point we can efficiently diverge into separate directions, thereby giving us three discrete series of analogs. Several palladium coupling methods are imnplemented to accomplish this. First, a Buchwald coupling[13] is used to access the morpholine analog 24a. This method can be succesfully used with any primary amine, secondary amine or aryl amine. Second, Stille and Suzuki couplings have are used to couple tribtyltin and phenylborate to produce the alkenyl and aryl substitutions, 24c and 24b, respectively. After coupling, the remainder of the molecule can be constructed as previously demonstrated to give compounds 26a–c. These methods can be used in combination to include any substitutent at C-5.

Scheme 6. manipulation of the 2′ and 3′ sugar hydroxy

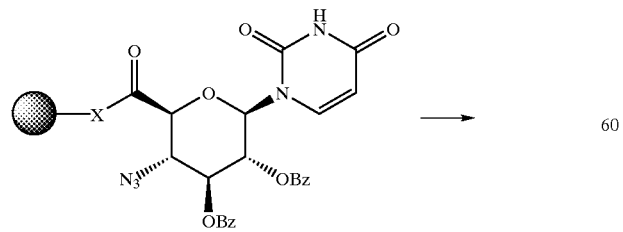

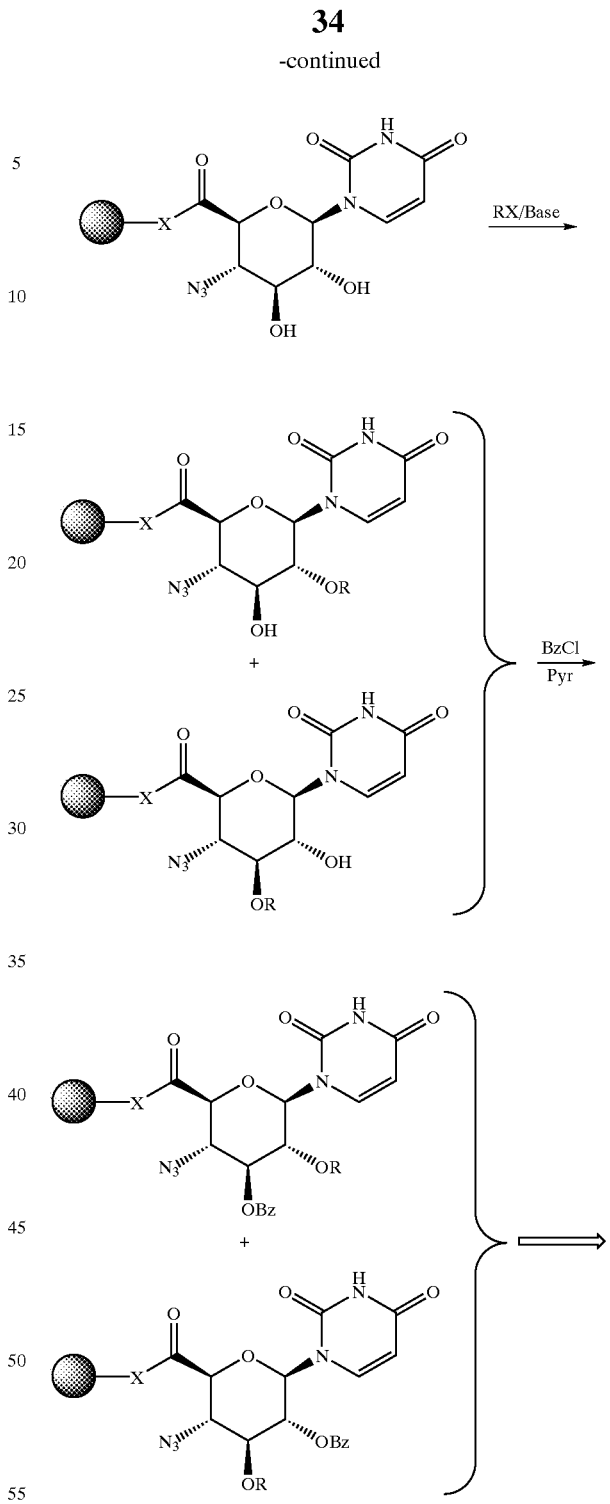

Functionalize as in previous examples

Compound 22 may be used to further functionalize the 2′ and 3′ sugar hydroxyls according to methods known in the art, and as depicted in Scheme 6.

Scheme 7. manipulation of the 2' and 3' sugar hydroxy

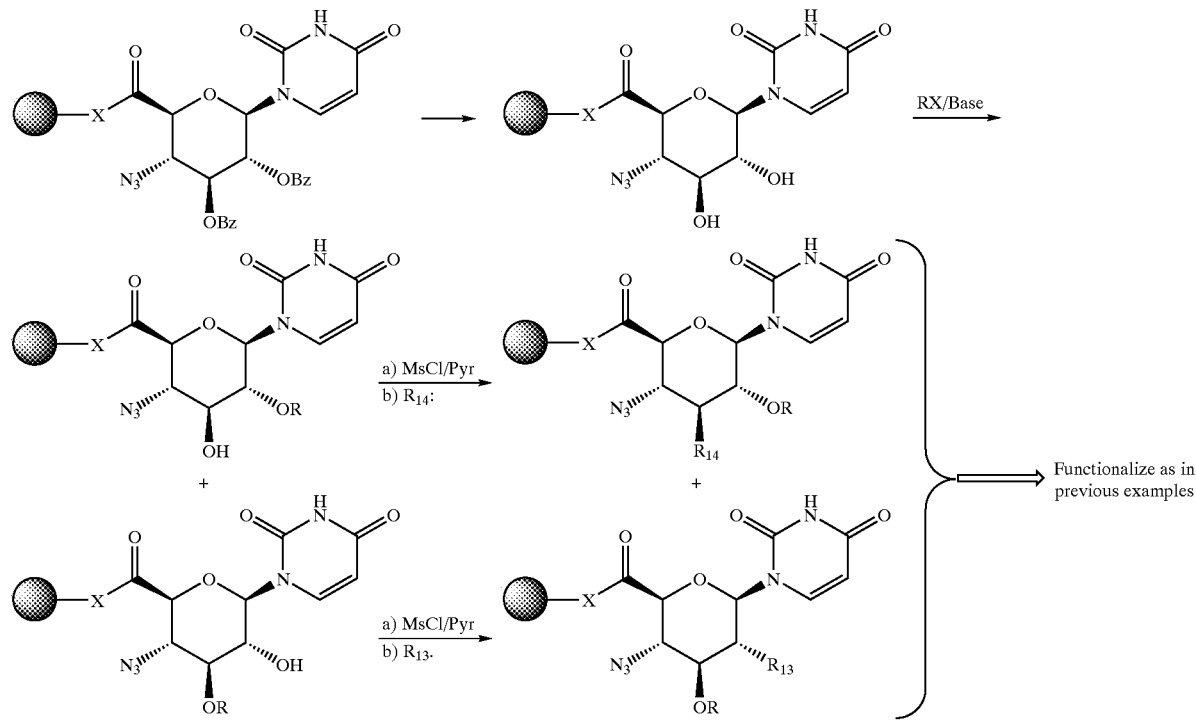

Compound 22 may be used to further functionalize or replace the 2' and 3' sugar hydroxyls according to methods known in the art, and as depicted in Scheme 7. The resultant compounds may be further chemically manipulated according to methods known in the art and according to methods of the present invention depicted in Schemes 1–5.

TABLE 1

Selected Examples.

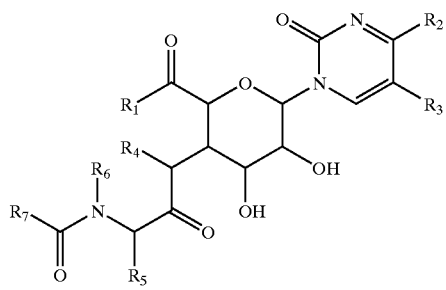

| Mass Spec Results | $R_1$ | $R_5$ | $R_7$ |
|---|---|---|---|
| 511 (M + H, 100)(M + Na, 78) | piperazine | L-diaminobutyryl | 1-aminoacetyl |
| 559 (M + H, 100)(M + Na, 51) | piperazine | D-meta-aza-PHE | 1-aminoacetyl |
| 511 (M + H, 100)(M + Na, 57) | piperazine | D-diaminobutyric acid | 1-aminoacetyl |
| 573 (M + H, 81)(M + Na, 35) | piperazine | 3-(3-pyridyl)-D-ALA | sarcosyl |
| 551 (M + H, 73)(M + Na, 58) | piperazine | R-2-piperidylglycine | 1-aminoacetyl |
| 525 (M + H, 100)(M + Na, 43) | piperazine | L-diaminobutyryl | sarcosyl |
| 539 (M + H, 100)(M + Na, 60) | piperazine | D-ORN | sarcosyl |
| 525 (M + H, 99)(M + Na, 35) | piperazine | D-ORN | 1-aminoacetyl |
| 551 (M + H, 100)(M + Na, 26) | piperazine | D-Ala-3-S-pyrrolidinyl | 1-aminoacetyl |
| 559 (M + H, 100)(M + Na, 39) | piperazine | 3-(3-pyridyl)-D-ALA | 1-aminoacetyl |
| 525 (M + H, 100)(M + Na, 55) | piperazine | D-diaminobutyric acid | sarcosyl |
| 551 (M + H, 100)(M + Na, 57) | piperazine | S-2-piperidylglycine | 1-aminoacetyl |
| 553 (M + H, 100)(M + Na, 58) | piperazine | D-LYS | sarcosyl |
| 565 (M + H, 100)(M + Na, 28) | piperazine | D-Ala-3-S-pyrrolidinyl | sarcosyl |
| 539 (M + H, 100)(M + Na, 67) | piperazine | D-LYS | 1-aminoacetyl |
| 573 (M + H, 100)(M + Na, 30) | piperazine | D-meta-aza-PHE | sarcosyl |

TABLE 1-continued

Selected Examples.

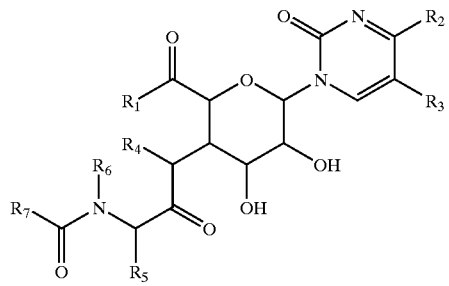

| Mass Spec Results | R₁ | R₅ | R₇ |
|---|---|---|---|
| 565 (M + H, 77)(M + Na, 43) | piperazine | R-2-piperidylglycine | sarcosyl |
| 565 (M + H, 91)(M + Na, 49) | piperazine | S-2-piperidylglycine | sarcosyl |
| 498 (M + H, 100)(M + Na, 66) | piperazine | D-SER | 1-aminoacetyl |
| 512 (M + H, 100)(M + Na, 60) | piperazine | D-SER | sarcosyl |
| 510 (2.45 min, 71%) | piperazine | AIB | sarcosyl |
| 524 (3.9 min, 58%) | piperazine | D-LEU | 1-aminoacetyl |
| 524 (3.88 min, 74%) | piperazine | D-LEU | 1-aminoacetyl |
| 538 (3.79 min, 63%) | piperazine | D-LEU | sarcosyl |
| 538 (3.78 min, 71%) | piperazine | D-LEU | sarcosyl |
| 496 (4.09 min, 58%) | piperazine | D-2-aminobutyryl | 1-aminoacetyl |
| 511 (4.63 min, 48%) | piperazine | D-diaminobutyric acid | 1-aminoacetyl |
| 510 (3.98 min, 66%) | piperazine | D-2-aminobutyryl | sarcosyl |
| 526 (4.09 min, 67%) | piperazine | D-(Allo)THR | sarcosyl |
| 512 (4.18 min, 65%) | piperazine | D-THR | 1-aminoacetyl |
| 510 (4.02 min, 61%) | piperazine | D-VAL | 1-aminoacetyl |
| 511 (M + H, 100)(M + Na, 78) | piperazine | L-diaminobutyryl | 1-aminoacetyl |
| 559 (M + H, 100)(M + Na, 51) | piperazine | D-meta-aza-PHE | 1-aminoacetyl |
| 511 (M + H, 100)(M + Na, 57) | piperazine | D-diaminobutyric acid | 1-aminoacetyl |
| 573 (M + H, 81)(M + Na, 35) | piperazine | 3-(3-pyridyl)-D-ALA | sarcosyl |
| 551 (M + H, 73)(M + Na, 58) | piperazine | R-2-piperidylglycine | sarcosyl |
| 525 (M + H, 100)(M + Na, 43) | piperazine | L-diaminobutyryl | sarcosyl |
| 539 (M + H, 100)(M + Na, 60) | piperazine | D-ORN | sarcosyl |
| 525 (M + H, 99)(M + Na, 35) | piperazine | D-ORN | 1-aminoacetyl |
| 551 (M + H, 100)(M + Na, 26) | piperazine | D-Ala-3-S-pyrrolidinyl | 1-aminoacetyl |
| 559 (M + H, 100)(M + Na, 39) | piperazine | 3-(3-pyridyl)-D-ALA | 1-aminoacetyl |
| 525 (M + H, 100)(M + Na, 55) | piperazine | D-diaminobutyric acid | sarcosyl |
| 551 (M + H, 100)(M + Na, 57) | piperazine | S-2-piperidylglycine | 1-aminoacetyl |
| 553 (M + H, 100)(M + Na, 58) | piperazine | D-LYS | sarcosyl |
| 565 (M + H, 100)(M + Na, 28) | piperazine | D-Ala-3-S-pyrrolidinyl | sarcosyl |
| 539 (M + H, 100)(M + Na, 67) | piperazine | D-LYS | 1-aminoacetyl |
| 573 (M + H, 100)(M + Na, 30) | piperazine | D-meta-aza-PHE | sarcosyl |
| 565 (M + H, 77)(M + Na, 43) | piperazine | R-2-piperidylglycine | sarcosyl |
| 565 (M + H, 91)(M + Na, 49) | piperazine | S-2-piperidylglycine | sarcosyl |
| 498 (M + H, 100)(M + Na, 66) | piperazine | D-SER | 1-aminoacetyl |
| 512 (M + H, 100)(M + Na, 60) | piperazine | D-SER | sarcosyl |
| 429 (M + H, 100)(M + Na, 72) | Amino | D-SER | 1-aminoacetyl |
| 442 (M + H, 100)(M + Na, 46) | Amino | D-diaminobutyric acid | 1-aminoacetyl |
| 496 (M + H, 100)(M + Na, 45) | Amino | S-2-piperidylglycine | sarcosyl |
| 456 (M + H, 100)(M + Na, 78) | Amino | D-ORN | 1-aminoacetyl |
| 482 (M + H, 100)(M + Na, 43) | Amino | S-2-piperidylglycine | 1-aminoacetyl |
| 470 (M + H, 100)(M + Na, 42) | Amino | D-ORN | sarcosyl |
| 504 (M + H, 78)(M + Na, 38) | Amino | 3-(3-pyridyl)-D-ALA | sarcosyl |
| 482 (M + H, 100)(M + Na, 20) | Amino | D-Ala-3-S-pyrrolidinyl | 1-aminoacetyl |
| 482 (M + H, 100)(M + Na, 60) | Amino | R-2-piperidylglycine | 1-aminoacetyl |
| 490 (M + H, 100)(M + Na, 45) | Amino | D-meta-aza-PHE | 1-aminoacetyl |
| 490 (M + H, 100)(M + Na, 51) | Amino | 3-(3-pyridyl)-D-ALA | 1-aminoacetyl |
| 470 (M + H, 100)(M + Na, 49) | Amino | D-LYS | 1-aminoacetyl |
| 496 (M + H, 100)(M + Na, 70) | Amino | R-2-piperidylglycine | sarcosyl |
| 443 (M + H, 100)(M + Na, 46) | Amino | D-SER | sarcosyl |
| 456 (M + H, 100)(M + Na, 60) | Amino | L-diaminobutyryl | sarcosyl |
| 504 (M + H, 100)(M + Na, 35) | Amino | D-meta-aza-PHE | sarcosyl |
| 442 (M + H, 100)(M + Na, 69) | Amino | L-diaminobutyryl | 1-aminoacetyl |
| 456 (M + H, 100)(M + Na, 50) | Amino | D-diaminobutyric acid | sarcosyl |
| 496 (M + H, 100)(M + Na, 13) | Amino | D-Ala-3-S-pyrrolidinyl | sarcosyl |
| 484 (M + H, 100)(M + Na, 44) | Amino | D-LYS | sarcosyl |
| 413 (3.71 min, 61%) | Amino | D-ALA | 1-aminoacetyl |
| 413 (3.5 min, 52%) | Amino | D-ALA | 1-aminoacetyl |
| 427 (3.25 min, 51%) | Amino | D-2-aminobutyryl | 1-aminoacetyl |
| 441 (2.89 min, 81%) | Amino | D-2-aminobutyryl | sarcosyl |
| 441 (2.91 min, 70%) | Amino | D-2-aminobutyryl | sarcosyl |

TABLE 1-continued

Selected Examples.

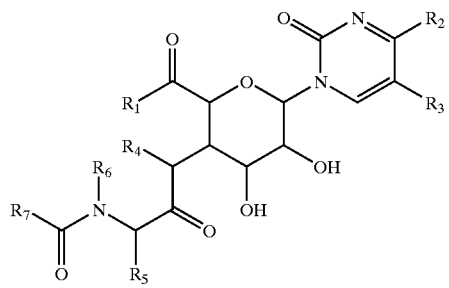

| Mass Spec Results | $R_1$ | $R_5$ | $R_7$ |
|---|---|---|---|
| 441 (2.65 min, 48%) | Amino | AIB | sarcosyl |
| 455 (3.41 min, 64%) | Amino | D-VAL | sarcosyl |
| 455 (3.43 min, 51%) | Amino | D-VAL | sarcosyl |
| 442 (4.28 min, 40%) | Amino | D-diaminobutyric acid | 1-aminoacetyl |
| 443 (3.31 min, 61%) | Amino | D-SER | sarcosyl |
| 457 (3.62 min, 71%) | Amino | D-THR | sarcosyl |
| 457 (3.86 min, 29%) | Amino | D-THR | sarcosyl |
| 428 (4.27 min, 47%) | Amino | D-Dap | 1-aminoacetyl |
| 428 (2.87 min, 51%) | Amino | D-Dap | 1-aminoacetyl |
| 429 (M + H, 100)(M + Na, 72) | Amino | D-SER | 1-aminoacetyl |
| 442 (M + H, 100)(M + Na, 46) | Amino | D-diaminobutyric acid | 1-aminoacetyl |
| 496 (M + H, 100)(M + Na, 45) | Amino | S-2-piperidylglycine | sarcosyl |
| 456 (M + H, 100)(M + Na, 78) | Amino | D-ORN | 1-aminoacetyl |
| 482 (M + H, 100)(M + Na, 43) | Amino | S-2-piperidylgiycine | 1-aminoacetyl |
| 470 (M + H, 100)(M + Na, 42) | Amino | D-ORN | sarcosyl |
| 504 (M + H, 78)(M + Na, 38) | Amino | 3-(3-pyridyl)-D-ALA | sarcosyl |
| 482 (M + H, 100)(M + Na, 20) | Amino | D-Ala-3-S-pyrrolidinyl | 1-aminoacetyl |
| 482 (M + H, 100)(M + Na, 60) | Amino | R-2-piperidylglycine | 1-aminoacetyl |
| 490 (M + H, 100)(M + Na, 45) | Amino | D-meta-aza-PHE | 1-aminoacetyl |
| 490 (M + H, 100)(M + Na, 51) | Amino | 3-(3-pyridyl)-D-ALA | 1-aminoacetyl |
| 470 (M + H, 100)(M + Na, 49) | Amino | D-LYS | 1-aminoacetyl |
| 496 (M + H, 100)(M + Na, 70) | Amino | R-2-piperidylglycine | sarcosyl |
| 443 (M + H, 100)(M + Na, 46) | Amino | D-SER | sarcosyl |
| 456 (M + H, 100)(M + Na, 60) | Amino | L-diaminobutyryl | sarcosyl |
| 504 (M + H, 100)(M + Na, 35) | Amino | D-meta-aza-PHE | sarcosyl |
| 442 (M + H, 100)(M + Na, 69) | Amino | L-diaminobutyryl | 1-aminoacetyl |
| 456 (M + H, 100)(M + Na, 50) | Amino | D-diaminobutyric acid | sarcosyl |
| 496 (M + H, 100)(M + Na, 13) | Amino | D-Ala-3-S-pyrrolidinyl | sarcosyl |
| 484 (M + H, 100)(M + Na, 44) | Amino | D-LYS | sarcosyl |

Additional examples of compounds according to the present invention are presented in Table 2.

TABLE 2

Selected Examples.

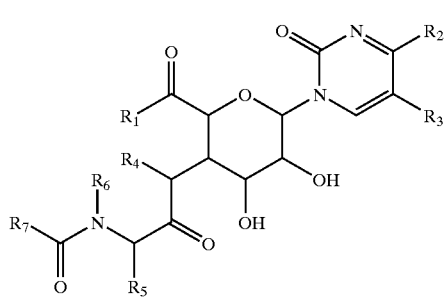

| $R_1$ | $R_2$ | $R_3$ |
|---|---|---|
|  | H | H |
| $NH_2$ | alkyl | H |

TABLE 2-continued

Selected Examples.

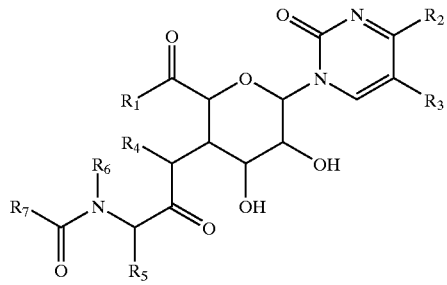

| $R_1$ | $R_2$ | $R_3$ |
|---|---|---|
| $NH_2$ | alkyl | alkyl |
| $N(alkyl)_2$ | $N(alkyl)_2$ | H |
| $N(alkyl)_2$ | $N(alkyl)_2$ | alkyl |
| $NH_2$ | $N(alkyl)_2$ | H |
| 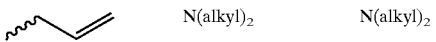 | $N(alkyl)_2$ | $N(alkyl)_2$ |

TABLE 2-continued

Selected Examples.

| $R_1$ | $R_2$ | $R_3$ |
|---|---|---|
| $NH_2$ | $N(alkyl)_2$ | H |
| (allyl) | $NH_2$ | H |
| (allyl) | $N(alkyl)_2$ | alkyl |

TABLE 3

Selected Examples.

| Mass Spec Results | $R_5$ | $R_2$ |
|---|---|---|
| 597 (2.45 min, 71%) | D-Ser | N,N-dimethyl-1,3-propanediamine |
| 567 | D-Dab | propylamine |
| 643 | D-Dab | 3,4-dimethylbenzylamino |
| 629 | D-Dab | Phenylethylamino |
| 602 | D-Ser | benzylamine |
| 676 | D-Dab | piperidinylpiperidinyl |
| 566 | D-Ser | Cyclopropylmethylamino |
| 605 | D-Dab | Furfurylamino |
| 583 | D-Dab | carboxylmethylamino |
| 662 | D-Dab | pyrrolidinylpiperidinyl |
| 622 | D-Dab | 2-(pyrrolidinyl)-1-ethylamino |
| 616 | D-Ser | Phenylethylamino |
| 636 | D-Dab | N-(3-aminopropyl)pyrrolidinyl |
| 579 | D-Dab | Cyclopropylmethylamino |
| 583 | D-Ser | (2-aminoethyl)dimethylamine |
| 581 | D-Dab | diethylamine |
| 553 | D-Dab | ethylamino |
| 663 | D-Ser | piperidinylpiperidinyl |
| 595 | D-Dab | morpholine |
| 610 | D-Dab | N,N-dimethyl-1,3-propanediamine |
| 568 | D-Ser | diethylamine |
| 540 | D-Ser | ethylamino |
| 630 | D-Ser | 3,4-dimethylbenzylamino |
| 665 | D-Dab | N-(3-aminopropane)piperidinyl |
| 582 | D-Ser | morpholine |

TABLE 3-continued

Selected Examples.

| Mass Spec Results | $R_5$ | $R_2$ |
|---|---|---|
| 596 | D-Dab | (2-aminoethyl)dimethylamine |
| 592 | D-Ser | Furfurylamino |
| 526 | D-Ser | Methylamine |
| 623 | D-Ser | N-(3-aminopropyl)pyrrolidinyl |
| 649 | D-Ser | pyrrolidinylpiperidinyl |
| 615 | D-Dab | benzylamine |
| 554 | D-Ser | propylamine |
| 581 | D-Ser | piperazine |
| 652 | D-Ser | N-(3-aminopropane)piperidinyl |
| 652 | D-Dab | N-(3-aminopropyl)morpholine |
| 639 | D-Ser | N-(3-aminopropyl)morpholine |
| 570 | D-Ser | carboxylmethylamino |
| 594 | D-Dab | piperazine |
| 609 | D-Ser | 2-(pyrrolidinyl)-1-ethylamino |
| 539 | D-Dab | Methylamine |

Tables 1 and 3 give examples of compounds prepared according to methods of the present invention, including LC/MS identification. Table 2 presents a broader class of compounds that could be prepared according to methods of the present invention through methods and techniques known in the art and presented herein.

Experimental:

Vorbruggen reaction (General Procedure). To a 1 litre round bottom flask under argon is added a nitrogenous base in dichloroethane or acetonitrile. Bis(trimethylsilyl)-acetamide (BSA, 15 mL) is added dropwise to the suspension and heated at 60° C. until a clear solution is formed. A second solution of azido sugar (6, 14.7 g) in dichloroethane (100 mL) or acetonitrile (100 mL) is treated with a lewis acid for 20 min. and then the silylated nitrogenous base is added. The mixture is heated for 2 days at 65° C. and then evaportaed under reduced pressure. The resultant solid is purified on silica gel, eluting with 10% methanol in dichloromethane.

Example 1

N-Acetyl cytidine (7.8 g) is reacted in dichloroethane (500 mL) with tin(IV)chloride (13 mL), according to the general procedure to give compound 7a.

Example 2

Uracil (3.0 g) is reacted in acetonitrile (300 mL) with trimethylsilyltriflate (TMS-OTf, 14.5 mL), according to the general procedure to give compound 7b.

Deprotection of Acetates (General Procedure). To a stirred solution of Et3N (9.5 mL) in methanol (2 mL) is added the hexopyranosyl nucleoside. After stirring for 24 h, the solution is evaporated under reduced pressure to dryness and the resultant solid is treated with Et2O (300 mL). The solids are then collected by vacuume filtration to give the deproteced product.

Example 3

Compound 7a (20.4 g) is treated according to the general procedure to give compound 8a.

Example 4

Compound 7b (10.1 g) is treated according to the general procedure to give compound 8b.

Radical Mediated Oxidation (General Procedure). To a stirred suspension of the primary alchohol in CH3CN (80 mL) and H2O (60 mL) is added iodobenzene diacetate (BLAB, 10.4 g) and TEMPO free radical (460 mg). The mixture is stirred for 4 hours at room temperature.

Example 5

Compound 8a (7.8 g) is treated according to the general procedure, and then worked up by filtration of the resultant precipitate to give compound 9a.

Example 6

Compound 8b (7.5 g) is treated according to the general procedure, and then worked up by evaporation under reduced pressure, followed by treatment with Et2O and collection of the resultant precipitate to give compound 9b.
Protection of Exocyclic Amine (Compound 10). To a stirred suspension of compound 9a (1.8 g) in CH3CN (22 mL) is added diisopropylethylamine (DIPEA, 1.62 mL) and 2-(trimethylsilyl)ethoxycarbonyl succinate (Teoc-OSu, 1.98 g). This solution is heated at 65° C. for 2 days and then evaporated to dryness under reduced pressure. The resultant solid is purified on silica gel, eluting with 10% methanol in CH2Cl 2 to give compound 10.
Loading of Precursor onto resin (General Procedure). A preformed solution of carboxylic acid, HATU (276 mg), diisopropylethylamine (DIPEA, 384 uL) in DMF (4 mL) is added to the resin. The mixture is gently agitated under argon for 12 hours and then filtered through a course frit. The resin is washed successively with DMF (3x), MeOH (3x) and CH2Cl2 (3x) and then dried under reduced pressure at room temperature. If the resin shows a positive Kaiser test, the coupling is repeated.

Example 7

Compound 10 (378 mg) is reacted with Argogel piperazine resin (652 mg, 0.35 mm/g) to give the resin bound compound 11a.

Example 8

Compound 9b (350 mg) is reacted with Argogel piperazine resin (620 mg, 0.35 mm/g) to give the resin bound compound 11b.

Example 9

Compound 22 (450 mg) is reacted with Argogel piperazine resin (650 mg, 0.35 mm/g) to give the resin bound compound 23.

Azide reduction (General Procedure). The resin bound azide is treated with a premixed solution of PhSH (25 uL), Et3N (42 uL) and SnCl2 (11 mg) in CH2Cl2 (800 uL). After 1 h, the resin is filtered through a course frit, washed successively with 10% Et3N in DMF (3x), DMF (3x), MeOH (3x) and CH2Cl2 (3x). The resin is then carried immediately to the next step.

Example 10

Compound 11a (30 mg) is treated according to the general procedure to give resin bound amine 12a.

Example 11

Compound 11b (30 mg) is treated according to the general procedure to give resin bound amine 12b.
Reductive Amination (General Prodedure). The resin bound amine is treated with 1% formaldehde in MeOH (750 mL) and trimethylorthoformate (TMOF, 500 mL) at room temperature. After 4 h, the resin is filtered through a course frit, washed successively with DMF (3x), MeOH (3x) and CH2Cl2 (3x). The resin is then immediately treated with a solution of MeOH (1.4 mL), TMOF (0.6 mL), AcOH (100 uL) and Na(CN)BH3 (13 mg). After 12 h, the resin is filtered through a course frit, washed successively with DMF (3x), MeOH (3x) and CH2Cl2 (3x). The resin is then carried immediately to the next step.

Example 12

Compound 12a (25 mg) is treated according to the general procedure to give resin bound amine 12c.

Example 13

Compound 12b (25 mg) is treated according to the general procedure to give resin bound amine 12d.
Coupling of Fmoc-Amino Acid (General Procedure). The amino resin is treated with a preformed solution of Fmoc-amino acid, HATU (276 mg), collidine (400 uL) in DMF (4 mL) and gently agitated under argon for 12 hours. The resin is then filtered through a course frit and washed successively with DMF (3x), MeOH (3x) and CH2Cl2 (3x) and then dried under reduced pressure at room temperature.

Example 14

Compound 12a (30 mg) is treated with Fmoc-D-serine (266 mg) according to the general procedure to give resin bound compound 13a.

Example 15

Compound 12b (30 mg) is treated with Fmoc-D-serine (266 mg) according to the general procedure to give resin bound compound 13b

Example 16

Compound 12c (30 mg) is treated with Fmoc-D-serine (266 mg) according to the general procedure to give resin bound compound 13c

Example 17

Compound 12d (30 mg) is treated with Fmoc-D-serine (266 mg) according to the general procedure to give resin bound compound 13d
Removal of Fmoc Group and Coupling of Carboxylic Acid (General Procedure). The Fmoc protected resin is added to a solution of piperidine (100 uL) and DMF (900 uL) and gently agitated for 1 hour. The resin is then filtered through a course flit and washed successively with DMF (3x), MeOH (3x) and CH2Cl2 (3x). The resultant, washed resin is treated with a preformed solution of carboxylic acid, HATU (276 mg), collidine (400 uL) in DMF (4 mL) and gently agitated under argon for 12 hours. The resin is then filtered through a course frit and washed successively with DMF (3x), MeOH (3x) and CH2Cl2 (3x) and then dried under reduced pressure at room temperature.

Example 18

Compound 13a (20 mg) is treated with Boc-sarcosine (170 mg) according to the general procedure to give resin bound compound 15a.

Example 19

Compound 13b (20 mg) is treated with Boc-sarcosine (170 mg) according to the general procedure to give resin bound compound 15b.

Example 20

Compound 13c (20 mg) is treated with Boc-sarcosine (170 mg) according to the general procedure to give resin bound compound 15c.

Example 21

Compound 13d (20 mg) is treated with Boc-sarcosine (170 mg) according to the general procedure to give resin bound compound 15d.
Debenzoylation and Cleavage from Resin (General Procedure). The resin is treated with 0.4M NaOH (aq, 100 uL) and MeOH (400 uL) and gently agitated for 4 hours. The resin is then filtered through a course frit and washed successively with MeOH (3×), DMF (3×), AcOH (3×) and CH2Cl2 (3×). The resin is then treated with 5% triisopropylsilane in trifluoroacetic acid (1 mL) for 4 hours. The resin is then filtered through a course frit and the acid is evaporated to dryness to give the final compound as a TFA salt.

Example 22

Resin 15a (20 mg) is treated according to the general procedure to give compound 17a.

Example 23

Resin 15b (20 mg) is treated according to the general procedure to give compound 17b.

Example 24

Resin 15c (20 mg) is treated according to the general procedure to give compound 17c.

Example 25

Resin 15d (20 mg) is treated according to the general procedure to give compound 17d.
Triazoylation of Uracil bound Resin and Nucleophilic Displacement (General procedure) 1,2,4-triazole (1.98 g), in CH3CN (25 mL) is treated with POCl3 (600 mL) and the reaction mixture is cooled down to 0° C. Et3N is then added dropwise over 10 minutes. The reaction is allowed to proceed at 0° C. for 30 min and then resin 11b (2.2 g) is added in one portion. The mixture is gently agitated under argon for 4 hours and then filtered through a course frit. The resin is washed successively with CH3CN (3×), CH2Cl2 (3×), MeOH (3×), DMF (3×) and CH2Cl2 (3×). A small portion of the resin is immediately treated with 10% amine in 1,4-dioxane (v/v). The mixture is gently agitated under argon for 12 hours and then filtered through a course frit. The resin is washed successively with DMF (3×), MeOH (3×) and CH2Cl2 (3×) and then dried under reduced pressure at room temperature.

Example 26

Resin 11b is treated according to the general procedure and 30 mg is removed for treatment with propylamine to give resin 19a. Further treatment of resin 19a according to the general procedures for azide reduction, amino acid coupling, Fmoc removal, acid coupling, debenzoylation and deprotection gives compound 21a as a TFA salt.

Example 27

Resin 11b is treated according to the general procedure and 30 mg is removed for treatment with benzylamine to give resin 19b. Further treatment of resin 19b according to the general procedures for azide reduction, amino acid coupling, Fmoc removal, acid coupling, debenzoylation and deprotection gives compound 21b as a TFA salt.

Example 28

Resin 11b is treated according to the general procedure and 30 mg is removed for treatment with morpholine to give resin 19c. Further treatment of resin 19c according to the general procedures for azide reduction, amino acid coupling, Fmoc removal, acid coupling, debenzoylation and deprotection gives compound 21c as a TFA salt.
Buchwald Coupling (General Procedure). Bromo resin 23 was treated with BINAP (0.3 M), NaOtBu (0.9 M), Pd2dba3 (0.01 M), and amine in N-methylpyrrolidinone (2 mL). The mixture is sealed and gently agitated at 80° C. for 24 hours. The resin is then filtered through a course frit and washed successively with MeOH (3×), DMF (3×), AcOH (3×), isopropanol (3×) and CH2Cl2 (3×). The resin is then treated with 5% triisopropylsilane in trifluoroacetic acid (1 mL) for 4 hours. The resin is then filtered through a course frit and the acid is evaporated to dryness to give the final compound as a TFA salt.
Stille Coupling (General Procedure). Bromo resin 23 was treated with TFP (1 mg), LiCl (8 mg), Pd2dba3 (5 mg) and N-methylpyrrolidinone (4 mL). After 15 min of gentle agitation, trialkyl tin is added via syringe. The mixture is sealed and gently agitated for 24 hours. The resin is then filtered through a course flit and washed successively with MeOH (3×), DMF (3×), and CH2Cl2 (3×). The resin is then treated with 5% triisopropylsilane in trifluoroacetic acid (1 mL) for 4 hours. The resin is then filtered through a course flit and the acid is evaporated to dryness to give the final compound as a TFA salt.
Suzuki Coupling (General Procedure). Bromo resin 23 was treated with Na2CO3 (aq, 2 M), Pd2dba3 (0.017M), the boronic acid and dimethoxyethane (2 mL). The mixture is sealed and gently agitated at 80° C. for 24 hours. The resin is then filtered through a course frit and washed successively with MeOH (3×), DMF (3×), AcOH (3×), and CH2Cl2 (3×). The resin is then treated with 5% triisopropylsilane in trifluoroacetic acid (1 mL) for 4 hours. The resin is then filtered through a course flit and the acid is evaporated to dryness to give the final compound as a TFA salt.

Example 29

Resin 23 (100 mg) is treated with morpholine (40 uL) according to the general procedure for Buchwald coupling to give compound 24a.

Example 30

Resin 23 (100 mg) is treated with trimethylphenyltin (30 uL) according to the general procedure for Stille coupling to give compound 24b.

Example 31

Resin 23 (100 mg) is treated with 2-thiophene boronic acid (0.06M in ethanol) according to the general procedure for Buchwald coupling to give compound 24c.

Example 32

Coupled Bacterial Transcription/Translation Assay

The DNA template, pBestLuc™ (Promega), is a plasmid containing a reporter gene for firefly luciferase fused to a strong tac promoter and ribosome binding site. Messenger RNA from 1 μg pBestLuc is transcribed and translated in *E. coli* S30 bacterial extract in the presence or absence of test compound. Compounds are tested in a black 96 well microtiter plate with an assay volume of 35 μL. Each test well contains: 5 μL test compound, 13 μL S30 premix (Promega), 4 μL 10×complete amino acid mix (1 mM each), 5 μL *E. coli* S30 extract and 8 μL of 0.125 μg/μL pBestLuc™. The transcription/translation reaction is incubated for 35 minutes at 37° C. followed by detection of functional luciferase with the addition of 30 μL LucLite™ (Packard). Light output is quantitated on a Packard TopCount.

Example 33

In Vitro Antibacterial Activity Determination of Minimum Inhibitory Concentrations (MICs)

The assays are carried out in 150 μL volume in duplicate in 96-well clear flat-bottom plates. The bacterial suspension from an overnight culture growth in appropriate medium is added to a solution of test compound in 4% DMSO in water. Final bacterial inoculum is approximately $10^5$–$10^6$ CFU/well. The percent growth of the bacteria in test wells relative to that observed for a well containing no compound is determined by measuring absorbance at 595 nm ($A_{595}$) after 24 h. The MIC is determined as a range of single compound where the complete inhibition of growth is observed at the higher concentration and cells are viable at the lower concentrations. Both ampicillin and tetracycline are used as antibiotic-positive controls in each screening assay for *S. pyogenes, E. coli, S. aureus, E. faecalis, K. pneumoniae* and *P. vulgaris*. Ciprofloxacin is used as an antibiotic positive control in each screening assay for *P. aeruginosa*.

Biological activity of selected compounds according to the present invention were assayed according to techniques known in the art. The results of these assays corresponding to synthesized compounds according to the present claims are presented in table 3.

TABLE 4

Biological activity of selected examples.

| No. | $R_5$ | $R_1$ | T/T (μM) | MIC(μM) |
|---|---|---|---|---|
| 1 | HO-CH(CH₂)-NH-C(=O)-CH₂-NH-CH₃ | piperazine (NH) | <0.4 | >200 |
| 2 | HO-CH(CH₂)-NH-C(=O)-CH₂-NH-CH₃ | piperazine (NH) | 10 | >200 |
| 3 | HO-CH(CH₂)-NH-C(=O)-CH₂-NH-CH₃ | NH₂ | <0.4 | >200 |

TABLE 4-continued

Biological activity of selected examples.

| No. | R₅ | R₁ | T/T (μM) | MIC (μM) |
|---|---|---|---|---|
| 4 | HO-CH₂-CH(NH-CO-CH₂-NH-CH₃)- | NH₂ | 0.4 | >200 |
| 5 | HO-CH₂-CH(NH-CO-CH₂-NH-H)- | piperazinyl | 2.1 | >100 |
| 6 | HO-CH₂-CH(NH-CO-CH₂-NH-H)- | NH₂ | 4.1 | >100 |
| 7 | HO-CH₂-CH(NH-CO-CH₂-NH-CH₂CH₃)- | piperazinyl | 5.3 | >100 |
| 8 | HO-CH₂-CH(NH-CO-CH₂-NH-CH₂CH₃)- | NH₂ | 1.7 | >100 |

TABLE 4-continued

Biological activity of selected examples.

| No. | R$_5$ | R$_1$ | T/T (μM) | MIC(μM) |
|---|---|---|---|---|
| 9 | H$_3$C-CH(NH-CO-CH$_2$-NH-CH$_3$)- | piperazin-1-yl (NH) | 3.2 | >100 |
| 10 | H$_3$C-CH(NH-CO-CH$_2$-NH-CH$_3$)- | NH$_2$ | 0.96 | >100 |
| 11 | H$_2$N-CH$_2$-CH(NH-CO-CH$_2$-NH-CH$_2$-CH$_3$)- | piperazin-1-yl (NH) | 0.36 | >100 |
| 12 | H$_2$N-CH$_2$-CH(NH-CO-CH$_2$-NH-CH$_2$-CH$_3$)- | NH$_2$ | 0.26 | >100 |

TABLE 4-continued

Biological activity of selected examples.

| No. | R₅ | R₁ | T/T (μM) | MIC (μM) |
|-----|----|----|----------|----------|
| 13 | H₂N-CH(~)-NH-C(=O)-CH₂-NH-CH₂-CH₃ | piperazin-1-yl (N-H) | 0.83 | >100 |
| 14 | H₂N-CH(~)-NH-C(=O)-CH₂-NH-CH₂-CH₃ | NH₂ | 0.75 | >100 |
| 15 | H₂N-CH(~)-NH-C(=O)-CH₂-NH-CH₂-CH₃ | piperazin-1-yl (N-H) | 1.7 | >100 |
| 16 | H₂N-CH(~)-NH-C(=O)-CH₂-NH-CH₂-CH₃ | NH₂ | 0.97 | >100 |

TABLE 4-continued

Biological activity of selected examples.

[Structure: pyranose ring with R1-C(=O)- group, cytosine base (with R2 at position 4), two OH groups, and NH-C(=O)-R5 substituent]

| No. | R₅ | R₁ | T/T (μM) | MIC (μM) |
|-----|----|----|----------|----------|
| 17 | H₂N-CH(–)-NH-C(=O)-CH₂-NH-CH₂-CH₃ | piperazinyl (NH) | 2.1 | >100 |
| 18 | H₂N-CH(–)-NH-C(=O)-CH₂-NH-CH₂-CH₃ | NH₂ | >10 | >100 |
| 19 | H₃C-CH(–)-NH-C(=O)-CH₂-NH-CH₃ | piperazinyl (NH) | 0.3 | >100 |
| 20 | H₂N-CH₂-CH₂-CH(–)-NH-C(=O)-CH₂-NH-CH₃ | NH₂ | 0.19 | >100 |

TABLE 4-continued

Biological activity of selected examples.

| No. | R₅ | R₁ | T/T ($\mu$M) | MIC ($\mu$M) |
|---|---|---|---|---|
| 21 | H₂N-CH(NHC(O)CH₂NHCH₃)-CH₂CH₂- | piperazine (N-linked) | 0.49 | 100 |
| 22 | H₂N-CH(NHC(O)CH₂NHCH₃)-CH₂CH₂- | NH₂ | 0.37 | 100 |
| 23 | NH₂-CH₂CH₂-CH(NHC(O)CH₂NHCH₃)- | piperazine (N-linked) | 0.25 | 50–75 |
| 24 | NH₂-CH₂CH₂-CH(NHC(O)CH₂NHCH₃)- | NH₂ | 0.03 | |
| 25 | NH₂-CH₂CH₂-CH(NHC(O)CH₂NH₂)- | piperazine (N-linked) | 0.26 | |
| 26 | NH₂-CH₂CH₂-CH(NHC(O)CH₂NH₂)- | NH₂ | 0.30 | |

TABLE 4-continued

Biological activity of selected examples.

| No. | R₅ | R₁ | T/T (μM) | MIC (μM) |
|---|---|---|---|---|
| 27 | H₂N-CH(NHC(O)CH₂NHCH₃)-(CH₂)₃- | piperazine | 0.23 | 100–150 |
| 28 | H₂N-CH(NHC(O)CH₂NHCH₃)-(CH₂)₃- | NH₂ | 0.20 | |
| 29 | H₂N-CH(NHC(O)CH₂NH₂)-(CH₂)₃- | NH₂ | 0.04 | |
| 30 | H₂N-CH(NHC(O)CH₂NH₂)-(CH₂)₃- | piperazine | 0.19 | 75–100 |
| 31 | HOCH₂-CH(NHC(O)CH₂NHCH₃)- | NH₂ | 0.33 | |
| 32 | HOCH₂-CH(NHC(O)CH₂NHCH₃)- | piperazine | <1 | |

TABLE 4-continued

Biological activity of selected examples.

| No. | R$_5$ | R$_1$ | T/T (μM) | MIC (μM) |
|---|---|---|---|---|
| 33 | H$_2$N-(chain)-NH-C(O)-CH$_2$-NH-CH$_3$ | NH$_2$ | 0.02 | |
| 34 | H$_2$N-(chain)-NH-C(O)-CH$_2$-NH-CH$_3$ | piperazinyl | 0.29 | 75–100 |
| 35 | H$_2$N-(chain)-NH-C(O)-CH$_2$-NH$_2$ | NH$_2$ | 0.19 | |
| 36 | H$_2$N-(chain)-NH-C(O)-CH$_2$-NH$_2$ | piperazinyl | 0.25 | 75–100 |

TABLE 4-continued

Biological activity of selected examples.

| No. | R₅ | R₁ | T/T (μM) | MIC(μM) |
|-----|----|----|----------|---------|
| 37 | (pyrrolidine-CH₂-CH(~)-NH-C(O)-CH₂-NH₂) | NH₂ | 0.13 | |
| 38 | (pyrrolidine-CH₂-CH(~)-NH-C(O)-CH₂-NH₂) | piperazine | 0.36 | |
| 39 | (pyrrolidine-CH₂-CH(~)-NH-C(O)-CH₂-NH-CH) | NH₂ | 0.18 | |
| 40 | (pyrrolidine-CH₂-CH(~)-NH-C(O)-CH₂-NH-CH) | piperazine | 0.18 | |
| 41 | (HO-CH₂-CH(~)-NH-C(O)-CH₂-NH₂) | NH₂ | 0.37 | |
| 42 | (HO-CH₂-CH(~)-NH-C(O)-CH₂-NH₂) | piperazine | 0.49 | |

*T/T is the abbreviation for "inhibition of bacterial Transcription/Translation."

Table 5 presents additional biological data for additional selected compounds according to the present invention.

TABLE 5

| No. | R$_2$ | R | T/T (uM) | MIC (uM) |
|---|---|---|---|---|
| 43 | -NH-CH$_2$CH$_2$CH$_2$-OH | CH$_2$NH$_2$ | 1.5 | >100 |
| 44 | | OH | 10–100 | >100 |
| 45 | -NH-CH$_2$-CH(OH)-CH$_3$ | CH$_2$NH$_2$ | 10–100 | >100 |
| 46 | | OH | 10–100 | >100 |
| 47 | CH$_3$-NH-CH$_2$-CH(OH)-CH$_3$ | CH$_2$NH$_2$ | 0.9 | >100 |
| 48 | | OH | 10–100 | >100 |
| 49 | H$_2$N-CH$_2$-CH(OH)-CH$_2$-OH | CH$_2$NH$_2$ | 2.1 | >100 |
| 50 | | OH | 10–100 | >100 |
| 51 | -NH-CH$_2$CH$_2$CH$_2$-N(piperazine)-N-CH$_3$ | CH$_2$NH$_2$ | 0.5 | 50–100 |
| 52 | | OH | 0.9 | >100 |
| 53 | -NH-CH$_2$CH$_2$-OH | CH$_2$NH$_2$ | 0.9 | >100 |
| 54 | | OH | 10–100 | >100 |
| 55 | -NH-CH$_2$CH$_2$-S-CH$_3$ | CH$_2$NH$_2$ | 1.2 | >100 |
| 56 | | OH | 18 | >100 |

TABLE 6

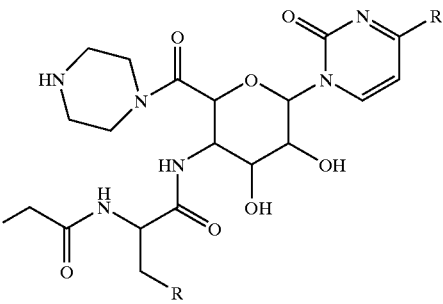

| No. | R₂ | R | T/T (uM) | MIC (uM) |
|---|---|---|---|---|
| 57 | ~NH-CH₂CH₂-pyrrolidine | CH₂NH₂ | 0.6 | 50–100 |
| 58 |  | OH | 10–100 | >100 |
| 59 | ~NH-(CH₂)₃-NMe₂ | CH₂NH₂ | 0.2 | 50–100 |
| 60 |  | OH | 0.6 | >100 |
| 61 | ~NH-(CH₂)₃-morpholine | CH₂NH₂ | 0.6 | 50–100 |
| 62 |  | OH | 1.6 | >100 |
| 63 | ~NH-(CH₂)₃-pyrrolidine | CH₂NH₂ | 0.4 | 50–100 |
| 64 |  | OH | 1.2 | >100 |
| 65 | ~NH-CH₂CH₂-NMe₂ | CH₂NH₂ | 0.5 | 50–100 |
| 66 |  | OH | 10–100 | >100 |
| 67 | ~NH-CH₂-COOH | CH₂NH₂ | 0.4 | >100 |
| 68 |  | OH | 10–100 | >100 |
| 69 | ~NH-OH | CH₂NH₂ | 0.9 | >100 |
| 70 |  | OH | 1.3 | >100 |

TABLE 7

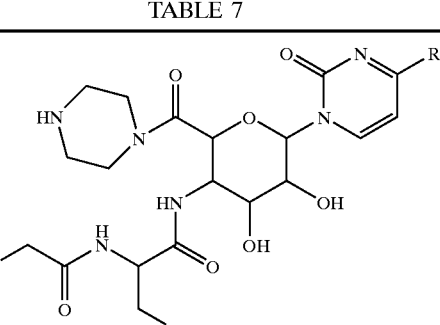

| No. | R₂ | R | T/T (uM) | MIC (uM) |
|---|---|---|---|---|
| 71 | ~NH-NH₂ | CH₂NH₂ | 10–100 | >100 |
| 72 |  | OH | 10–100 | >100 |

TABLE 7-continued

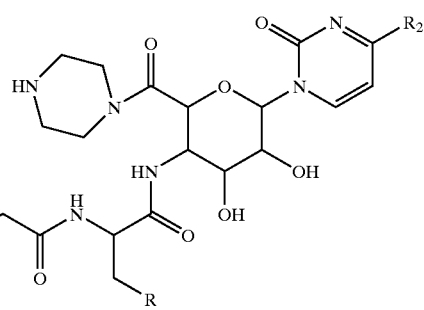

| No. | R₂ | R | T/T (uM) | MIC (uM) |
|---|---|---|---|---|
| 73 | ~NH-OMe | CH₂NH₂ | 10–100 | >100 |
| 74 |  | OH | 10–100 | >100 |
| 75 | ~N-piperidine-pyrrolidine | CH₂NH₂ | 1.0 | >100 |
| 76 |  | OH | >100 | >100 |
| 77 | ~N-piperidine-piperidine | CH₂NH₂ | 10–100 | >100 |
| 78 |  | OH | 10–100 | >100 |
| 79 | ~N(Et)₂ | CH₂NH₂ | 1.2 | >100 |
| 80 |  | OH | 2.2 | >100 |
| 81 | ~N-morpholine | CH₂NH₂ | 10–100 | >100 |
| 82 |  | OH | 10–100 | >100 |
| 83 | ~N-piperazine | CH₂NH₂ | 10–100 | >100 |
| 84 |  | OH | >100 | >100 |

TABLE 8

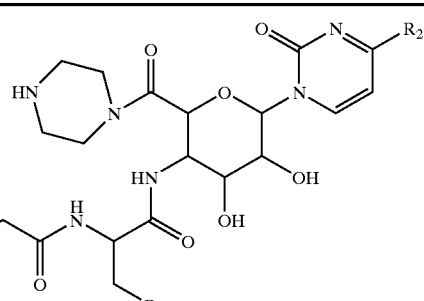

| No | R₂ | R | T/T (uM) | MIC (uM) |
|---|---|---|---|---|
| 85 | ~NH-iPr | CH₂NH₂ | 2.0 | >100 |
| 86 |  | OH | 10–100 | >100 |

TABLE 8-continued
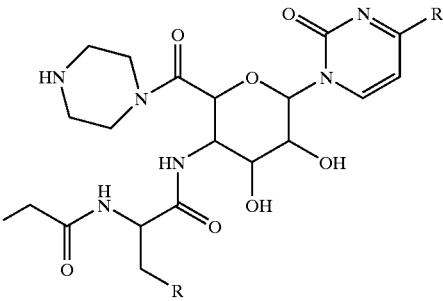
| No | R₂ | R | T/T (uM) | MIC (uM) |
|---|---|---|---|---|
| 87 | 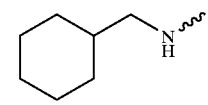 | CH₂NH₂ | 10–100 | >100 |
| 88 | | OH | 10–100 | >100 |
| 89 | 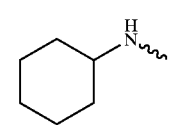 | CH₂NH₂ | 4.6 | 50–100 |
| 90 | | OH | 10–100 | >100 |
| 91 | 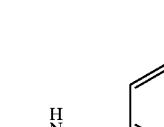 | CH₂NH₂ | 0.5 | 25–50 |
| 92 | | OH | 0.7 | >100 |
| 93 | 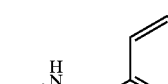 | CH₂NH₂ | 0.4 | 50–100 |
| 94 | | OH | 10–100 | >100 |
| 95 | 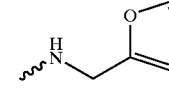 | CH₂NH₂ | 0.4 | 50–100 |
| 96 | | OH | 0.6 | >100 |
| 97 | 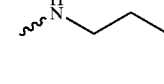 | CH₂NH₂ | 0.5 | 25–50 |
| 98 | | OH | 2.3 | >100 |
| 99 | 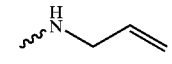 | CH₂NH₂ | 10–100 | >100 |
| 100 | | OH | 10–100 | >100 |
| 101 | 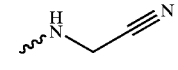 | CH₂NH₂ | 1.5 | 50–100 |
| 102 | | OH | 10–100 | >100 |
TABLE 9
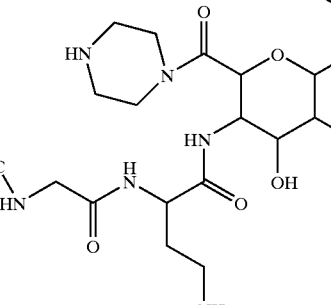
| No. | R₂ | MIC (E. Coli Pathogenic) |
|---|---|---|
| 103 | 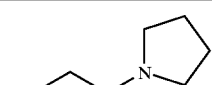 | 50–100 uM |
| 104 | 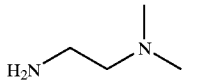 | 50–100 uM |
| 105 |  | 50–100 uM |
| 106 | 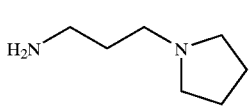 | 50–100 uM |
| 107 | 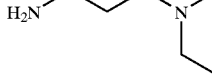 | 50–100 uM |
| 108 | 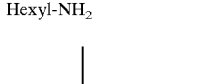 | 50–100 uM |
| 109 | Me-NH₂ | >100 uM |
| 110 | Et-NH₂ | 50–100 uM |
| 111 | Pr-NH₂ | 50–100 uM |
| 112 | Bu-NH₂ | >100 uM |
| 113 | Pentyl-NH₂ | 50–100 uM |
| 114 | Hexyl-NH₂ | >100 uM |
| 115 | 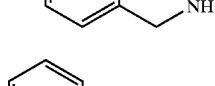 | 25–50 uM |
| 116 | 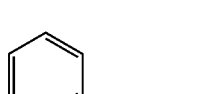 | 50–100 uM |
| 117 | 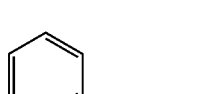 | 50–100 uM |

Table 10 presents results of activity assays for selected compounds against fungi, as exemplified by activity against *c. albicans* according to assays known in the art.

TABLE 10

| NO. | Compound | Activity against *C. Albicans* ($\mu M$) |
|---|---|---|
| 1 | | 1–3 |
| 2 | | 3–6 |
| 3 | | 6–12 |
| 4 | | 50–100 |

TABLE 10-continued

| NO. | Compound | Activity against *C. Albicans* (μM) |
|---|---|---|
| 5 | [structure] | 1–3 |
| 6 | [structure] | 1–3 |

What is claimed is:

1. A compound of the formula (I):

[structure I]

where
- $R_1$ is —$NR_8R_9$ or —$C(R_{10})_3$;
- $R_2$ is —$NR_{17}R_{18}$;
- $R_3$ and $R_7$ each independently are —$NR_{11}R_{12}$, —YZ, alkyl, substituted alkyl, cycloalkyl, aryl, heteroaryl, alkylenearyl, halo, or H radical;
- each $R_5$ independently is alkyl, substituted alkyl, cycloalkyl, aryl, heteroaryl, —$(CH_2)_nN(R_{11}R_{12})$, —$(CH_2)_nG$ or H;
- $R_6$ is an electron pair, alkyl, cycloalkyl, aryl, heteroaryl or H;
- $R_4$, $R_{11}$, $R_{12}$, $R_{15}$, $R_{16}$ and $R_{17}$ each independently are alkyl, cycloalkyl, aryl, heteroaryl or H;
- $R_8$ and $R_9$ each independently are alkyl, cycloalkyl, aryl, heteroaryl, H or together join to form an aminocyclic ring radical;
- each $R_{10}$ independently is alkyl, cycloalkyl, aryl, heteroaryl, halo or H;
- $R_{13}$ and $R_{14}$ are each hydroxyl;
- $R_{18}$ is alkyl, cycloalkyl, aryl, heteroaryl, 2-(dimethylamino)ethyl, propyl-$L_1$, or methyl-$L_2$ where $L_1$ is dimethylamino, 1-methylpiperazinyl, or pyrrolidinyl and $L_2$ is phenyl, 3,4-dimethylphenyl, 2-methylfuranyl, or cyano;
- Y is a heteroatom radical with Z a radical selected from the group comprising 1 or more heteroatoms or H, alkyl, cycloalkyl, aryl, heteroaryl, halo, combinations thereof and adapted to fill the valence of Y, said Y being singly or doubly bound to the pyrimidine ring radical;
- Q is a member selected from the group of radicals comprising —S(=O)—, —$S(O)_2$—, —C(=O)—, —C(=S)—, —$CH_2$—, —Y(O)— and —$C(Y)_n$—; where G is a cyclic alkyl or cyclic heteroalkyl substituent and n is an integer of at least 0; and with the proviso that;
- when $R_2$ is $NH_2$ and $R_9$ is H, then;
  - $R_8$ is not an amino acid and;
  - the ratio of carbon atoms to nitrogen atoms of $R_5$ is greater than or equal to one and;
  - $R_{16}$ is H radical and;
  - $R_{15}$ does not comprise a

[structure]

radical.

2. The compound according to claim 1 wherein $R_1$ is $N(alkyl)_2$;
- $R_2$ is NHalkyl; and
- $R_3$, $R_4$ and $R_7$ are H.

3. The compound according to claim 1 wherein;

R₁ is piperazine radical;

R₂ is

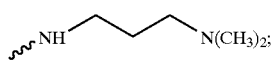

and

R₅ is (CH₂)₂OH.

4. The compound according to claim 3 wherein Q is a C(=O) radical.

5. The compound according to claim 3 wherein Q is a C(=S) radical.

6. The compound according to claim 3 wherein Q is a S(=O) radical.

7. The compound according to claim 1 wherein;

R₁ is a piperazine radical; and

R₂ is

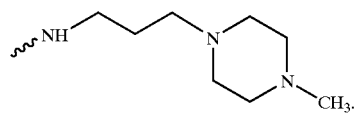

8. The compound according to claim 7 wherein Q is a C(=O) radical.

9. The compound according to claim 7 wherein Q is a C(=S) radical.

10. The compound according to claim 7 wherein Q is a S(=O) radical.

11. The compound according to claim 1 wherein;

R₁ is a piperazine radical; and

R₂ is

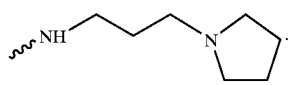

12. The compound according to claim 11 wherein Q is a C(=O) radical.

13. The compound according to claim 11 wherein Q is a C(=S) radical.

14. The compound according to claim 11 wherein Q is a S(=O) radical.

15. The compound according to claim 1 wherein;

R₁ is a piperazine radical; and

R₂ is

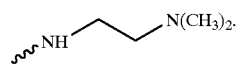

16. The compound according to claim 15 wherein Q is a C(=O) radical.

17. The compound according to claim 15 wherein Q is a C(=S) radical.

18. The compound according to claim 15 wherein Q is a S(=O) radical.

19. The compound according to claim 1 wherein;

R₁ is a piperazine radical; and

R₂ is

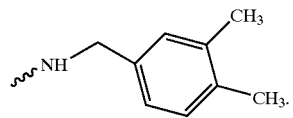

20. The compound according to claim 19 wherein Q is a C(=O) radical.

21. The compound according to claim 19 wherein Q is a C(=S) radical.

22. The compound according to claim 19 wherein Q is a S(=O) radical.

23. The compound according to claim 1 wherein;

R₁ is a piperazine radical; and

R₂ is

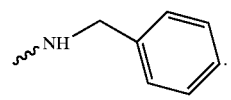

24. The compound according to claim 23 wherein Q is a C(=O) radical.

25. The compound according to claim 23 wherein Q is a C(=S) radical.

26. The compound according to claim 23 wherein Q is a S(=O) radical.

27. The compound according to claim 1 wherein;

R₁ is a piperazine radical; and

R₂ is

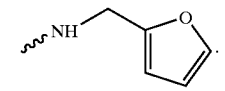

28. The compound according to claim 27 wherein Q is a C(=O) radical.

29. The compound according to claim 27 wherein Q is a C(=S) radical.

30. The compound according to claim 27 wherein Q is a S(=O) radical.

31. The compound according to claim 1 wherein;

R₁ is a piperazine radical; and

R₂ is

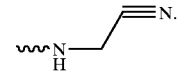

32. The compound according to claim 31 wherein is a C(=O) radical.

33. The compound according to claim 31 wherein Q is a C(=S) radical.

34. The compound according to claim 31 wherein Q is a S(=O) radical.

35. The compound of claim 1 having structure Ia;

Ia

36. The compound of claim 1 having structure Ib.

Ib

37. The compound of claim 1 wherein at least one stereoisomer is predominate.

38. A pharmaceutical composition comprising: a compound according to claim 1 and pharmaceutically acceptable salts thereof, associated with a pharmaceutically acceptable carrier, diluent, prodrug or lubricant.

39. A method of making compounds according to claim 1 comprising:
 a) associating a compound according to structure III where A is a linker and G is $N_3$, with a solid support for generating an intermediate compound associated with the solid support through said linker according to structure IIIa

III where ⬤ is the solid support;

IIIa b) generating the intermediate compound IIIa associated with the solid support;
 c) chemically manipulating said intermediate compound thereby generating the compound according to claim 1.

40. The method according to claim 39 wherein the intermediate is according to structure IV

IV

41. The method according to claim 39 wherein the solid support is a resin.

* * * * *

UNITED STATES PATENT AND TRADEMARK OFFICE
CERTIFICATE OF CORRECTION

PATENT NO. : 6,933,288 B2  
DATED : August 23, 2005  
INVENTOR(S) : Michael T. Migawa et al.

It is certified that error appears in the above-identified patent and that said Letters Patent is hereby corrected as shown below:

Column 73,  
Line 55, insert -- arylenealkyl -- between "alkylenearyl" and "halo";

Column 75,  
Line 2, insert -- a -- between "is" and "piperazine".

Signed and Sealed this

Sixth Day of June, 2006

JON W. DUDAS  
*Director of the United States Patent and Trademark Office*